(12) United States Patent
Bär et al.

(10) Patent No.: US 6,489,327 B1
(45) Date of Patent: Dec. 3, 2002

(54) TRYPTASE INHIBITORS

(75) Inventors: Thomas Bär; Thomas Martin; Josef Stadlwieser; Wolf-Rüdiger Ulrich, all of Constance; Andreas Dominik, Allensbach; Ulrich Thibaut, Constance; Daniela Bundschuh, Constance; Rolf Beume, Constance; Karl-Josef Goebel, Radolfzell; Wolfram Bode, Gauting; Luis Moroder, Martinsried; Pedro Jose Barbosa Pereira, Krailling; Andreas Bergner, Neuried; Robert Huber, Germering; Christian Sommerhoff; Norbert Schaschke, both of München, all of (DE)

(73) Assignees: Max-Planck-Gesellschaft zur Fordrungder Wisenschaften, e.V., Munich (DE); Byk Gulden Lomberg Chemische Fabrik GmbH, Constance (DE)

( * ) Notice: Subject to any disclaimer, the term of this patent is extended or adjusted under 35 U.S.C. 154(b) by 0 days.

(21) Appl. No.: 09/601,317

(22) PCT Filed: Feb. 4, 1999

(86) PCT No.: PCT/EP99/00726

§ 371 (c)(1),
(2), (4) Date: Oct. 20, 2000

(87) PCT Pub. No.: WO99/40083

PCT Pub. Date: Aug. 12, 1999

(30) Foreign Application Priority Data

Feb. 6, 1998 (DE) .......................... 198 04 761
Nov. 6, 1998 (DE) .......................... 198 51 299

(51) Int. Cl.[7] .................... A61K 31/495; C07D 241/02; C07D 295/00; C07D 213/00
(52) U.S. Cl. ...................... 514/252.11; 514/252.13; 514/255.01; 514/255.05; 544/357; 544/358; 544/398; 544/402; 546/1; 546/186; 546/244; 546/246; 546/248

(58) Field of Search ............................... 544/357, 358, 544/398, 402; 546/1, 186, 244, 246, 248; 514/252.11, 252.13, 255.01, 255.05

(56) References Cited

FOREIGN PATENT DOCUMENTS

| DE | 3600387 | * | 2/1987 |
| JP | 61215360 | * | 9/1986 |
| WO | 9532945 | * | 12/1995 |
| WO | 96 09297 | | 3/1996 |
| WO | 9804537 | * | 2/1998 |

OTHER PUBLICATIONS

Rice et al., "Inhibitors of Tryptase for the treatment of Mast Cell–Mediated Diseases", Curr. Pharm. Des., vol. 4, No. 5, May 1998, pp. 381–396.

Caughey et al., "Bis(5–Amidino–2–Benzimidazolyl)Methane and related am idines. Are Potent, Reversible Inhibitors of Mast Cell Tryptaes", Journal of Pharmacology and Experimental Therapeutics, vol. 264, No. 2, Jan. 1, 1993, pp. 676–682.

Stürzebecher et al., "Inhibition of Human Mast Cell Tryptase by Benzamidine Derivatives", Biol. Chem. Hoppe– Seyler, vol. 373, Oct. 1992, pp. 1025–10303.

Goodson et al., "The Chem otherapyh of Amoebiasis. III. Variants of Bis(diamylamino)decane", Br.J.Pharmacol., vol. 3, 1948, pp. 62–71.

* cited by examiner

Primary Examiner—Mukund J. Shah
Assistant Examiner—Sudhaker B. Patel
(74) Attorney, Agent, or Firm—Arent Fox Kintner Plotkin & Kahn

(57) ABSTRACT

The invention relates to novel inhibitors of human tryptase which are used in the pharmaceutical industry for the production of medicaments.

10 Claims, 12 Drawing Sheets

Pyridine-2,6-dicarbobis[4-(aminomethylbenzoyl)-1-piperazide] (1)

Figure 1:
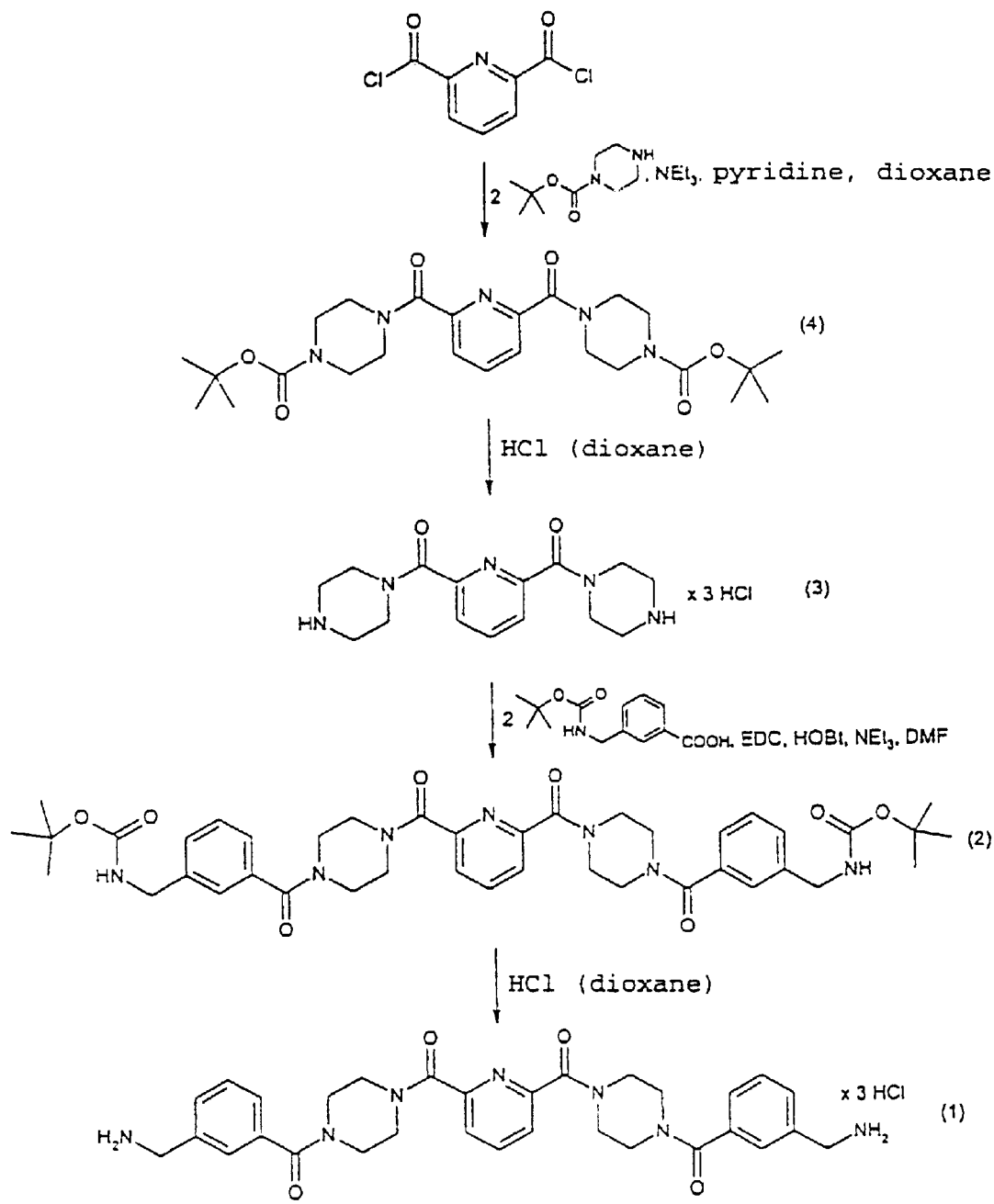

Pyridine-2,6-dicarbobis[4-(trans-4-amino-methylcyclohexylcarbonyl)-1-piperazide] (5)

2,6-Dimethyl-4-phenylpyridine-3,5-dicarbobis[4-(3-aminomethylbenzoyl)-1-piperazide] (7)

Pyridine-2,6-dicarbobis[4-(3-aminomethylbenzoylamino)-1-piperidide] (11)

Pyridine-2,6-dicarbobis[4-(4-aminomethyl-cyclohexylcarbonylamino)-1-piperidide] (15)

Bis{4-[4-(4-aminomethylcyclohexanoyl)piperazin-1-yl]carbonyl}-4,4'-diaminodiphenyl ether dihydrochloride (17)

Bis{4-[4-(3-aminomethyl)benzoylpiperazin-1-yl]carbonyl}-4,4'-diaminodiphenyl ether dihydrochloride (21)

Di{4-[4-(4-aminomethyl)cyclohexanoylamino]piperidin-1-ylcarbamoyl}cyclohexylmethane dihydrochloride (23)

2,2-Bis{4-[4-(4-aminophenyl)-1-piperazinylcarbonyl-methoxy]phenyl}propane dihydrochloride (27)

2,2-Bis[4-(4-guanidylbenzylamino)carbonylmethoxyphenyl]propane dihydroacetate (31)

2,2-Bis[4-(10-amino-3,6-diaza-2,5-dioxodecyloxy)-phenyl}propane dihydrochloride (34)

2,2-Bis{4-[4-(4-aminomethylbenzylcarbamoyl)-1-piperazinylcarbonyloxy]phenyl}propane dihydrochloride (36)

TRYPTASE INHIBITORS

APPLICATION OF THE INVENTION

The invention relates to novel inhibitors of human tryptase which are used in the pharmaceutical industry for the production of medicaments.

KNOWN TECHNICAL BACKGROUND

Human tryptase is a serine proteinase which is the predominant protein present in human mast cells. The term tryptase covers four closely related enzymes (α, I, II/β, III; possessing 90 to 98% sequence identity) (cf. Miller et al., J. Clin. Invest. 84 (1989) 1188–1195; Miller et al., J. Clin. Invest. 86 (1990) 864–870; Vanderslice et al., Proc. Natl. Acad. Sci., USA 87 (1990) 3811–3815). With the exception of α-tryptase (Schwartz et al., J. Clin. Invest. 96 (1995) 2702–2710; Sakai et al., J. Clin. Invest. 97 (1996) 988–995), the enzymes are activated intracellularly and stored in catalytically active form in secretory granules.

As compared with other known serine proteinases, such as trypsin or chymotrypsin, tryptase exhibits some exceptional properties (Schwartz et al., Methods Enzymol. 244, (1994), 88–100; G. H. Caughey, "Mast cell proteases in immunology and biology." Marcel Dekker, Inc., New York, 1995). Tryptase obtained from human tissue has a noncovalently linked tetrameric structure which has to be stabilized by heparin or other proteoglycans in order to be proteolytically active.

Low-molecular-weight compounds are described as tryptase inhibitors in the international applications WO 95/32945, WO 96/09297 and WO 98/04537.

DESCRIPTION OF THE INVENTION

It has now been found that the compounds of the formula I described in more detail below possess surprising and particularly advantageous properties.

The invention relates to compounds of the formula I $$\begin{array}{c} B1-A1-B3-A3-B5-A5-K1 \\ / \\ M \\ \backslash \\ B2-A2-B4-A4-B6-A6-K2 \end{array} \quad (I)$$

in which

A1 and A2 are identical or different and are —C(O)—, —NH—, —O— (oxygen), —S— (sulfur), —S(O)$_2$—, —S(O)$_2$—NH—, —NH—S(O)$_2$—, —C(O)—NH—, —NH—C(O)—, —O—C(O)—, —C(O)—O— or a bond, A3 and A4 are identical or different and are —C(O)—, —C(S)—, —O—, —S—, —NH—, —O—C(O)—, —C(O)—O—, —C(O)—NH—, —NH—C(O)— or a bond, or are selected from the group

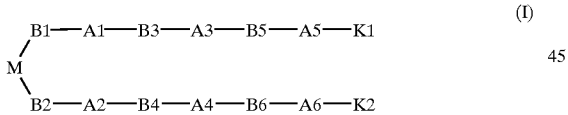

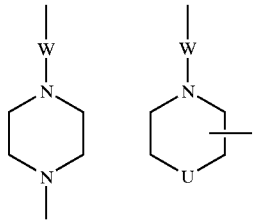

where

U is —O— (oxygen) or —CH$_2$— (methylene),

V is —O— (oxygen), —S— (sulfur) or —CH$_2$— (methylene), and

W is the group —C(O)— or a bond,

A5 and A6 are identical or different and are —C(O)—, —NH—, —O—, —S—, —C(O)—NH—, —NH—C(O)—, —O—C(O)—, —C(O)—O— or a bond, M is selected from one of the following groups

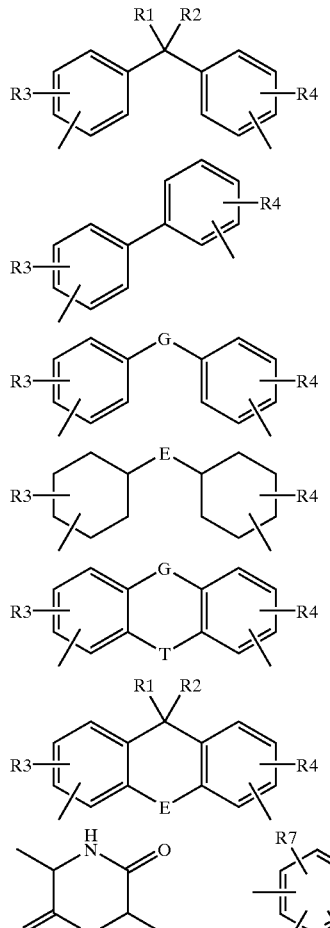

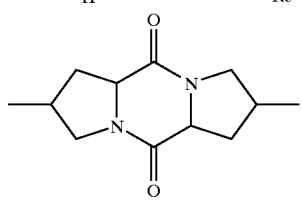

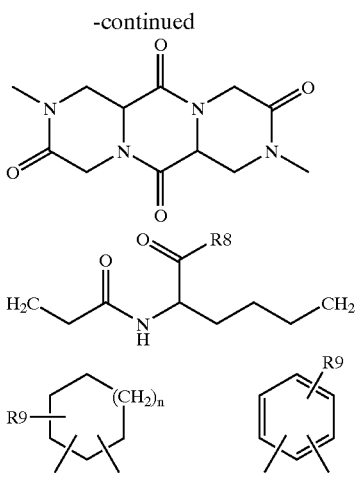

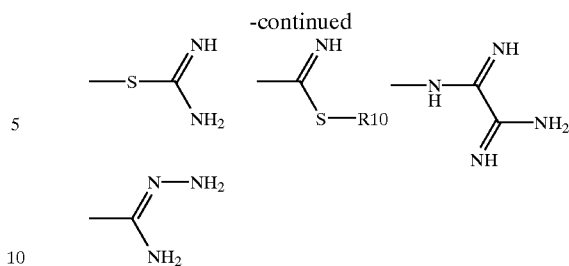

where
R1 and R2 are identical or different and are hydrogen, 1–4C-alkyl, 1–4C-alkyl which is wholly or partially substituted by fluorine, or hydroxyl, or R1 and R2 together, and including the carbon atom to which they are bonded, are —C(O)— or a 5- or 6-membered, optionally substituted cyclic hydrocarbon, R3 and R4 are identical or different and are hydrogen or one, two or three identical or different 1–4C-alkyl radicals, E is —CH$_2$—, —O— or a bond, G is —S—, —O— or —S(O)$_2$—, T is —CH$_2$—, —O— or a bond, R5 and R6 are identical or different and are hydrogen or 1–4C-alkyl, R7 is hydrogen, 1–4C-alkyl, phenyl or pyridyl, R8 is 1–4C-alkoxy, N(R81)R82, piperidino or morpholino, R81 and R82 are identical or different and are hydrogen or 1–4C-alkyl, R9 is hydrogen or one, two or three identical or different 1–4C-alkyl radicals, n is 0, 1, 2 or 3, K1 is -B7-(C(O))$_m$-B9-X1, -B7-(C(O))$_m$-B9-Y1 or -B7-(C(O))$_m$-B9-Z1-B11-X1, K2 is -B8-(C(O))$_p$-B10-X2, -B8-(C(O))$_p$-B10-Y2 or -B8-(C(O))$_p$-B10-Z2-B12-X2, B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and selected from the following groups

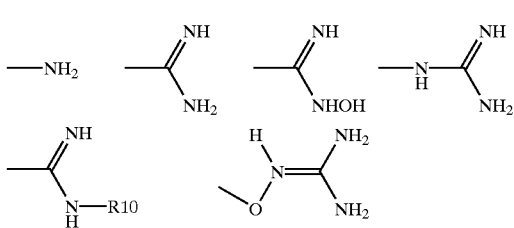

where
R10 is 1–4C-alkyl,

Y1 and Y2 are identical or different and are a 4–11C-heteroaryl or 2–7C-heterocycloalkyl radical which contains at least one ring nitrogen, Z1 and Z2 are identical or different and are 5–12C-arylene, 5–12C-heteroarylene, 3–8C-cycloalkylene or 3–8C-heterocycloalkylene, with each arylene, heteroarylene, cycloalkylene, heterocycloalkylene, heteroaryl or heterocycloalkyl additionally, for its part, being able to be substituted by one, two or three substituents selected from the group hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl, and in which 24 to 40 bonds must be present on the direct route between the terminal nitrogen atoms, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms, two carbonyl groups or one carbonyl group and one thiocarbonyl group.

1–4C-Alkyl represents straight-chain or branched alkyl radicals having from 1 to 4 carbon atoms. The butyl, the iso-butyl, the sec-butyl, the tert-butyl, the propyl, the isopropyl, the ethyl and the methyl radical may be mentioned by way of example.

Examples of 1–4C-alkyl which is entirely or partially substituted by fluorine which may be mentioned are the 2,2,3,3,3-pentafluoropropyl, the perfluoroethyl, the 1,2,2-trifluoroethyl, the 1,1,2,2-tetrafluoroethyl, the 2,2,2-trifluoroethyl, the trifluoromethyl and the difluoromethyl radicals.

Examples of a 5- or 6-membered cyclic hydrocarbon which may be mentioned are cyclopentane or cyclohexane.

1–4C-Alkoxy represents radicals which, in addition to the oxygen atom, contain a straight-chain or branched alkyl radical having from 1 to 4 carbon atoms. The butoxy, the iso-butoxy, the sec-butoxy, the tert-butoxy, the propoxy, the isopropoxy and, preferably, the ethoxy and the methoxy radical may be mentioned by way of example.

1–4C-Alkylene represents straight-chain or branched 1–4C-alkylene radicals, for example the methylene [—CH$_2$—], the ethylene [—CH$_2$—CH$_2$—], the trimethylene [—CH$_2$—CH$_2$—CH$_2$—], the tetramethylene [—CH$_2$—CH$_2$—CH$_2$—CH$_2$—], the 1,2-dimethylethylene [—CH(CH$_3$)—CH(CH$_3$)—], the 1,1-dimethylethylene [—C(CH$_3$)$_2$ —CH$_2$—], the 2,2-dimethylethylene [—CH$_2$—C(CH$_3$)$_2$—], the isopropylidene [—C(CH$_3$)$_2$—] or the 1-methylethylene [—CH(CH$_3$)—CH$_2$—] radical.

1–3C-Alkylene represents straight-chain or branched 1–3C-alkylene radicals, for example the methylene

[—CH₂—], the ethylene [—CH₂—CH₂—], the trimethylene [—CH₂—CH₂—CH₂—], the isopropylidene [—C(CH₃)₂—] or the 1-methylethylene [—CH(CH₃)—CH₂—] radical.

If m has the meaning 0, the group —(C(O))ₘ— is then a bond.

If p has the meaning 0, the group —(C(O))ₚ— is then a bond.

If n has the meaning 0, the group —(CH₂)ₙ— is then a bond.

4–11C-Heteroaryl is an optionally substituted monocyclic or bicyclic aromatic hydrocarbon which contains from 4 to 11 C atoms and at least one ring nitrogen atom; in addition, one or more of the carbon atoms can be replaced by ring heteroatoms selected from the group O, N or S. In bicycles, at least one of the rings is aromatic. Pyrid-4-yl, pyrid-3-yl, pyrimidin-5-yl, imidazol-1-yl and benzimidazol-5-yl may be mentioned by way of example.

2–7C-Heterocycloalkyl is an optionally substituted monocyclic saturated or partially saturated hydrocarbon which contains from 2 to 7 C atoms and at least one ring nitrogen atom; in addition, one or more carbon atoms can be replaced by ring heteroatoms selected from the group O, N or S. Piperid-4-yl, piperazin-1-yl, pyrrolidin-2-yl, pyrrolidin-3-yl, imidazolidin-1-yl, imidazolidin-2-yl, imidazolidin-4-yl and morpholin-2-yl may be mentioned by way of example.

5–12C-Arylene is an optionally substituted divalent monocyclic or bicyclic aromatic hydrocarbon radical which possesses from 5 to 12 C atoms, with at least one of the rings being aromatic in the case of the bicyclic aromatic hydrocarbon radicals. The free valencies can both be located on the aromatic ring or on the nonaromatic ring, or one can be located on the aromatic ring and one on the nonaromatic ring. 1,4-Phenylene, 1,3-phenylene, 1,4-naphthylene and 2,6-naphthylene may be mentioned by way of example.

5–12C-Heteroarylene is an arylene radical, as previously defined, in which from 1 to 4 C atoms are replaced by heteroatoms selected from the group O, N and S. 2,5-Furylene, 2,5-pyrrolylene, 4,2-pyridylene, 5,2-pyridylene, 2,5-indolylene, 2,6-indolylene, 3,5-indolylene, 3,6-indolylene, 3,5-indazolylene, 3,6-indazolylene, 2,5-benzofuranylene, 2,6-quinolinylene and 4,2-thiazolylene may be mentioned by way of example.

3–8C-Cycloalkylene is an, optionally substituted, divalent monocyclic or partially saturated hydrocarbon radical which possesses from 3 to 8 C atoms. The 1,3-cyclopentylene, the 1,3-cyclohexylene and, preferably, the 1,4-cyclohexylene radical may be mentioned by way of example.

3–8C-Heterocycloalkylene is a cycloalkylene radical, as previously defined, in which from 1 to 3 C atoms are replaced by heteroatoms selected from the group O, N and S. The 1,4-piperidinylene, the 1,4-piperazinylene, the 2,5-pyrrolidinylene, the 4,2-imidazolidinylene and, preferably, the 4,1-piperidinylene radical may be mentioned by way of example.

1–4C-Alkoxycarbonyl is a carbonyl group to which one of the abovementioned 1–4C-alkoxy radicals is bonded. The methoxycarbonyl (CH₃O—C(O)—) and the ethoxycarbonyl (CH₃CH₂O—C(O)—) radical may be mentioned by way of example.

1–4C-Alkylcarbonyloxy is a carbonyloxy group to which one of the abovementioned 1–4C-alkyl radicals is bonded. The acetoxy radical (CH₃C(O)—O—) may be mentioned by way of example.

Several of the groups listed under M possess, either in themselves or due to their substitution, one or more chiral centers. The invention therefore encompasses both all the pure enantiomers and all the pure diastereomers and also their mixtures in any mixing ratio.

The groups Z1 and Z2, respectively, are located, by definition, between the groups B9 and B11 (-B9-Z1-B11-) and B10 and B12 (-B10-Z2-B12-), respectively. Correspondingly, in the divalent groups (e.g. 2,6-indolylene) which are mentioned by way of example, the first number is that of the site for linkage to the B9 or B10 group, respectively, and the second number is that of the site for linkage to the B11 or B12 group, respectively.

In the context of this application, the expression "terminal nitrogen atom" in each case refers to a nitrogen atom in the groups denoted X1, X2, Y1 and Y2.

If the groups X1 and/or X2 contain only one nitrogen atom, this nitrogen atom is the terminal nitrogen atom.

If the groups X1 and/or X2 contain a plurality of nitrogen atoms, the nitrogen atom which is located furthest from the atom via which the bond to groups B9 (B11) or B10 (B12) is effected is the terminal nitrogen atom.

If the groups Y1 and/or Y2 contain only one ring nitrogen atom, this ring nitrogen atom is the terminal nitrogen atom.

If the groups Y1 and/or Y2 contain a plurality of ring nitrogen atoms, the ring nitrogen atom which is located furthest from the atom via which the bond with the groups B9 or B10 is effected is the terminal nitrogen atom.

According to the invention, the direct route between the nitrogen atoms which act as terminal nitrogen atoms in the groups defined as X1 (Y1) or X2 (Y2) is the number of bonds which is obtained by counting the bonds which represent the shortest possible link between the terminal nitrogen atoms.

The following example is used to illustrate how the number of bonds on the direct route between two terminal nitrogen atoms is determined:

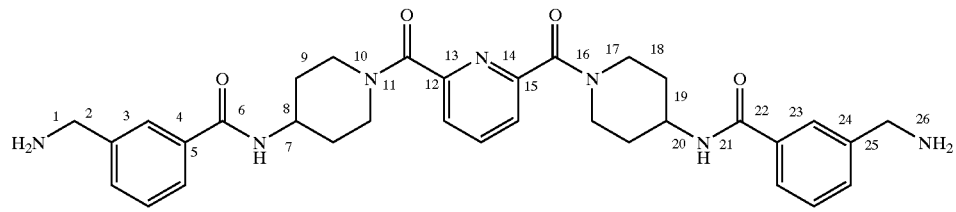

Here, the direct route encompasses 26 bonds.

The inhibitors according to the invention are bifunctional inhibitors, i.e. inhibitors having two reactive functional groups. These groups are such that they can bind specifically to active sites of tryptase. The two functional groups of the inhibitor preferably bind to active sites in different monomer subunits of the tryptase tetramer.

The inhibitors according to the invention are suitable for inhibiting human tryptase. Human tryptase is understood as meaning, in particular, the human enzyme β-tryptase with the EC No. 3.4.21.59.

Depending on substitution, all acid addition salts or all salts with bases are suitable salts for compounds of the formula I. Those which may in particular be mentioned are the pharmacologically tolerated salts of the inorganic and organic acids which are customarily used in pharmacy. Suitable salts of this nature are, on the one hand, water-soluble and water-insoluble acid addition salts with acids such as hydrochloric acid, hydrobromic acid, phosphoric acid, nitric acid, sulfuric acid, acetic acid, citric acid, D-gluconic acid, benzoic acid, 2-(4-hydroxybenzoyl) benzoic acid, butyric acid, sulfosalicylic acid, maleic acid, lauric acid, malic acid, fumaric acid, succinic acid, oxalic acid, tartaric acid, embonic acid, stearic acid, toluene-sulfonic acid, methanesulfonic acid or 3-hydroxy-2-naphthoic acid, with the acids being employed, when preparing the salt, in an equimolar quantity ratio or in a quantity ratio which differs from this depending on whether the acid is a monobasic or polybasic acid and on which salt is desired.

On the other hand, salts with bases are also suitable. Examples of salts with bases which may be mentioned are alkali (lithium, sodium or potassium) or calcium, aluminum, magnesium, titanium, ammonium, meglumin or guanidinium salts, with the bases also in this case being employed, when preparing the salt, in an equimolar quantity ratio, or in a quantity ratio which differs from this.

Salts which are not pharmacologically tolerated and which can, for example, initially arise as process products when producing the compounds according to the invention on an industrial scale, are converted into pharmacologically tolerated salts using methods known to the skilled person.

The skilled person knows that the compounds according to the invention, and also their salts, when they are isolated in crystalline form, for example, can contain varying quantities of solvents. The invention therefore also encompasses all solvates and, in particular, all hydrates of the compounds of the formula I, as well as all solvates and, in particular, all hydrates of the salts of the compounds of the formula I.

One embodiment (embodiment a) of the compounds according to the invention of the formula I is that in which A1 and A2 are identical or different and are —C(O)—, —NH—, —O— (oxygen), —S— (sulfur), —S(O)$_2$—, —S(O)$_2$—NH—, —NH—S(O)$_2$—, —C(O)—NH—, —NH—C(O)—, —O—C(O)—, —C(O)—O— or a bond, A3 and A4 are identical or different and are —C(O)—, —C(S)—, —O— —S—, —NH—, —O—C(O)—, —C(O)—O—, —C(O)—NH—, —NH—C(O)— or a bond, or are selected from the group

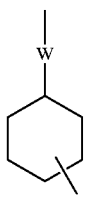 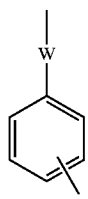 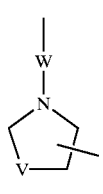

-continued

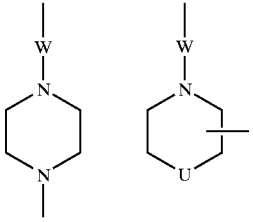

where
U is —O— (oxygen) or —CH$_2$— (methylene),
V is —O— (oxygen), —S— (sulfur) or —CH$_2$— (methylene), and
W is the group —C(O)— or a bond,
A5 and A6 are identical or different and are —C(O)—, —NH—, —O—, —S—, —C(O)—NH—, —NH—C(O)—, —O—C(O)—, —C(O)—O— or a bond,
M is selected from one of the following groups

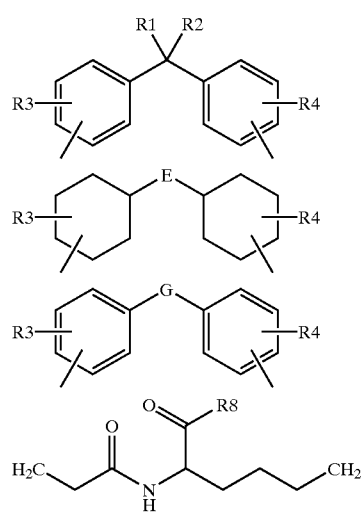

where
R1 and R2 are identical or different and are hydrogen, 1–4C-alkyl, 1–4C-alkyl which is wholly or partially substituted by fluorine, or hydroxyl, or R1 and R2 together, and including the carbon atom to which they are bonded, are —C(O)— or a 5- or 6-membered, optionally substituted cyclic hydrocarbon,
R3 and R4 are identical or different and are hydrogen or one, two or three identical or different 1–4C-alkyl radicals,
E is —CH$_2$—, —O— or a bond,
G is —S—, —O— or —S(O)$_2$—,
R8 is 1–4C-alkoxy, N(81)R82, piperidino or morpholino,
R81 and R82 are identical or different and are hydrogen or 1–4C-alkyl,
K1 is -B7-(C(O))$_m$-B9-X1, -B7-(C(O))$_m$-B9-Y1 or -B7-(C(O))$_m$-B9-Z1-B11-X1,
K2 is -B8-(C(O))$_p$-B10-X2, -B8-(C(O))$_p$-B10-Y2 or -B8-(C(O))$_p$-B10-Z2-B12-X2,
B1, B2, B3, B4, B5 and B6 are identical or different and are a bond or 1–4C-alkylene,
B7, B8, B9, B10, B11 and B12 are identical or different and are a bond or 1–3C-alkylene,
m is 0 or 1,
p is 0 or 1,
X1 and X2 are identical or different and are selected from the following groups

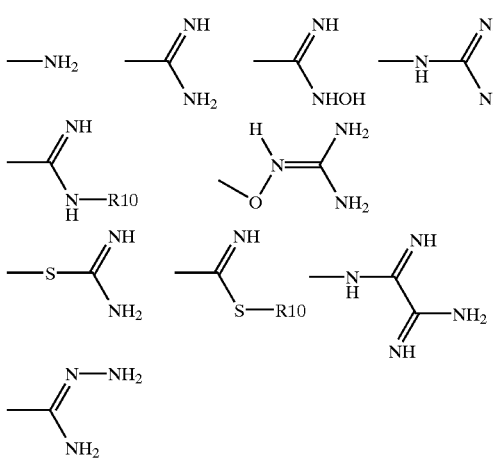
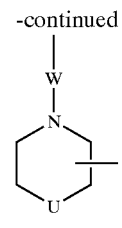

where
R10 is 1–4C-alkyl,
Y1 and Y2 are identical or different and are a 4–11C-heteroaryl or 2–7C-heterocycloalkyl radical which contains at least one ring nitrogen,
Z1 and Z2 are identical or different and are 5–12C-arylene, 5–12C-heteroarylene, 3–8C-cycloalkylene or 3–8C-heterocycloalkylene,
with each arylene, heteroarylene, cycloalkylene, heterocycloalkylene, heteroaryl or heterocycloalkyl additionally, for its part, being able to be substituted by one, two or three substituents selected from the group hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl,
and in which 24 to 40 bonds must be present on the direct route between the terminal nitrogen atoms,
the salts of these compounds, and also the N-oxides of the heteroaryls, heterocycloalkyls, heteroarylenes and heterocycloalkylenes which contain a nitrogen atom, and their salts,
with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms, two carbonyl groups or one carbonyl group and one thiocarbonyl group.

Compounds of embodiment a which are to be emphasized are those in which
A1 and A2 are identical or different and are —C(O)—, —NH—, —O— (oxygen), —C(O)—NH—, —NH—C(O)—, —O—C(O)—, —C(O)—O— or a bond,
A3 and A4 are identical or different and are —C(O)—, —O—, —NH—, —O—C(O)—, —C(O)—O—, —C(O)—NH—, —NH—C(O)— or a bond, or are selected from the group

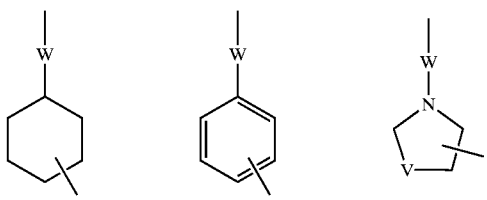

where
W is the group —C(O)— or a bond,
A5 and A6 are identical or different and are —C(O)—, —NH—, —O—, —C(O)—NH—, —NH—C(O)—, —O—C(O)—, —C(O)—O— or a bond,
M is selected from one of the following groups

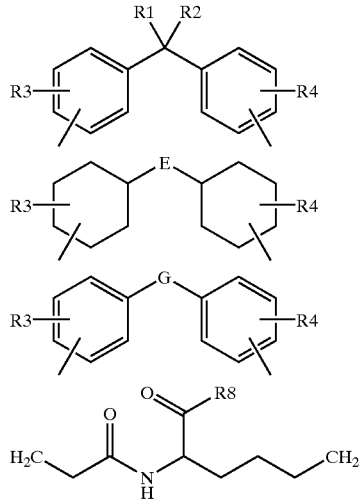

where
R1 and R2 are identical or different and are hydrogen, 1–4C-alkyl, 1–4C-alkyl which is wholly or partially substituted by fluorine, or hydroxyl, or R1 and R2 together, and including the carbon atom to which they are bonded, are —C(O)— or a 5- or 6-membered, optionally substituted cyclic hydrocarbon,
R3 and R4 are identical or different and are hydrogen or one, two or three identical or different 1–4C-alkyl radicals,
E is —CH$_2$—, —O— or a bond,
G is —S—, —O— or —S(O)$_2$—,
R8 is 1–4C-alkoxy, N(R81)R82, piperidino or morpholino,
R81 and R82 are identical or different and are hydrogen or 1–4C-alkyl,
K1 is -B7-(C(O))$_m$-B9-X1, -B7-(C(O))$_m$-B9-Y1 or -B7-(C(O))$_m$-B9-Z1-B11-X1,
K2 is -B8-(C(O))$_p$-B10-X2, -B8-(C(O))$_p$-B10-Y2 or -B8-(C(O))$_p$-B10-Z2-B12-X2,
B1, B2, B3, B4, B5 and B6 are identical or different and are a bond or straight-chain or branched 1–4C-alkylene,
B7, B8, B9, B10, B11 and B12 are identical or different and are a bond or 1–3C-alkylene,
m is 0 or 1,
p is 0 or 1,
X1 and X2 are identical or different and are selected from the following groups

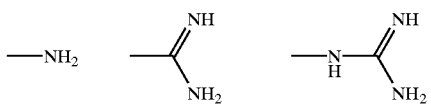 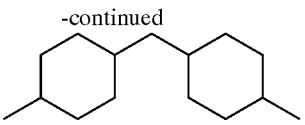

Y1 and Y2 are identical or different and are piperid-4-yl, piperid-3-yl, piperazin-1-yl, piperazin-2-yl, morpholin-2-yl, pyrrolidin-2-yl, pyrrolidin-3-yl, imidazolidin-1-yl, imidazolidin-2-yl, imidazolidin-4-yl, 2-imidazolin-3-yl, 2-imidazolin-2-yl, imidazol-1-yl, imidazol-2-yl, imidazol-4-yl, 5-methylimidazol-4-yl, pyrid-4-yl, pyrid-3-yl, pyridazin-4-yl, pyrimidin-5-yl, pyrimidin-4-yl, indol-3-yl, benzimidazol-4-yl or benzimidazol-5-yl, Z1 and Z2 are identical or different and are 1,4-phenylene, 1,3-phenylene, 1,4-naphthylene, 2,6-naphthylene, 1,4-cyclohexylene, 1,3-cyclohexylene, 1,3-cyclopentylene, 1,4-piperazinylene, 4,1-piperidinylene, 1,4-piperidinylene, 2,5-pyrrolidinylene, 4,2-imidazolidinylene, 2,5-furylene, 2,5-pyrrolylene, 4,2-pyridylene, 5,2-pyridylene, 6-methyl-5,2-pyridinylene, 2,5-indolylene, 2,6-indolylene, 3,5-indolylene, 3,6-indolylene, 3,5-indazolylene, 3,6-indazolylene, 2,6-quinolinylene, 2,5-benzofuranylene or 4,2-thiazolylene, and in which 24 to 40 bonds must be present on the direct route between the terminal nitrogen atoms, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms or carbonyl groups.

Compounds of embodiment a which are in particular to be emphasized are those in which A1 and A2 are identical or different and are —O— (oxygen) or —NH—C(O)—, A3 and A4 are identical or different and are —C(O)-NH— or are selected from the group

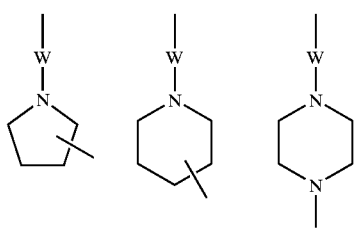

where W is the group —C(O)— or a bond,

A5 and A6 are identical or different and are —C(O)—, —C(O)—NH—, —NH—C(O)— or a bond, M is selected from one of the following groups

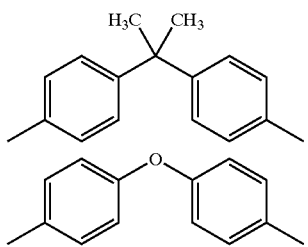

K1 is -B7-(C(O))$_m$-B9-X1 or -B7-(C(O))$_m$-B9-Z1-B11-X1,

K2 is -B8-(C(O))$_p$-B10-X2 or -B8-(C(O))$_p$-B10-Z2-B12-X2,

B1, B2, B3, B4, B5 and B6 are identical or different and are a bond or —CH$_2$— (methylene), B7, B8, B9, B10, B11 and B12 are identical or different and are a bond or 1–2C-alkylene, m is 0 or 1, p is 0 or 1, X1 and X2 are identical or different and are amino, amidino or guanidino, Z1 and Z2 are identical or different and are 1,4-phenylene, 1,3-phenylene, 1,4-cyclohexylene or 1,4-piperazinylene, and in which 24 to 40 bonds must be present on the direct route between the terminal nitrogen atoms, the salts of these compounds, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms or two carbonyl groups.

Preferred compounds of embodiment a are those in which

A1 and A2 are identical or different and are —O— (oxygen) or —NH—C(O)—,

A3 and A4 are identical or different and are —C(O)-NH— or are selected from the group

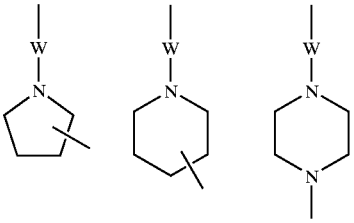

where W is the group —C(O)— or a bond,

A5 and A6 are identical or different and are —C(O)—, —NH—C(O)— or a bond,

M is selected from one of the following groups

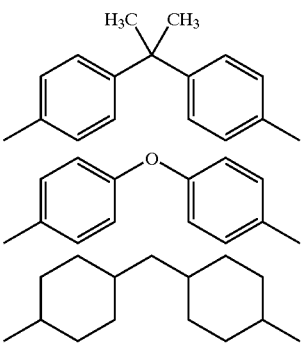

K1 is -B7-(C(O))$_m$-B9-Z1-B11-X1,

K2 is -B8-(C(O))$_p$-B10-Z2-B12-X2,

B1, B2, B3, B4, B5 and B6 are identical or different and are a bond or —CH$_2$— (methylene), B7, B8, B9, B10, B11 and B12 are identical or different and are a bond or —CH$_2$— (methylene), m is 0 or 1, p is 0 or 1, X1 and X2 are identical or different and are amino, amidino or guanidino, Z1 and Z2 are identical or different and are 1,4-phenylene, 1,3-phenylene, 1,4-cyclohexylene or 1,4-piperazinylene, and in which 24 to 40 bonds must be present on the direct route between the terminal nitrogen atoms, the salts of these compounds, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms or two carbonyl groups.

Particularly preferred compounds of embodiment a are bis{4-[4-(4-aminomethylcyclohexanoyl)piperazin-1-yl]-carbonyl}-4,4'-diaminodiphenyl ether, bis{4-[(3-aminomethyl)benzoylpiperazin-1-yl]carbonyl}-4,4'-diaminodiphenyl ether, di{4-[4-(4-aminomethyl)cyclohexanoyl-amino]piperidin-1-ylcarbamoyl}cyclohexylmethane, 2,2-bis[4-(4-guanidinylbenzylamino)carbonylmethoxyphenyl]-propane, 2,2-bis[4-(10-amino-3,6-diaza-2,5-dioxodecyloxyphenyl] propane and 2,2-bis{4-[4-(4-aminomethylbenzylcarbamoyl)-1-piperazinylcarbonyloxy]phenyl}propane, and also the salts of these compounds.

Another embodiment (embodiment b) of the compounds according to the invention of the formula I is that in which A1 and A2 are identical or different and are —C(O)—, —NH—, —O— (oxygen), —S— (sulfur), —S(O)₂—, —S(O)₂—NH—, —NH—S(O)₂—, —C(O)—NH—, —NH—C(O)—, —O—C(O)—, —C(O)—O- or a bond, A3 and A4 are identical or different and are —C(O)—, —C(S)—, —O—, —S—, —NH—, —O—C(O)—, —C(O)—O—, —C(O)—NH—, —NH—C(O)— or a bond, or are selected from the group

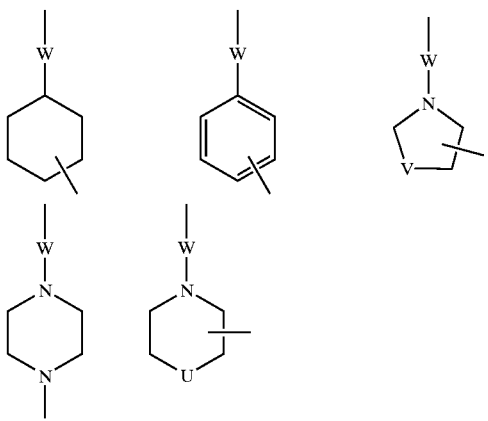

where

U is —O— (oxygen) or —CH₂— (methylene),

V is —O— (oxygen), —S— (sulfur) or —CH₂— (methylene), and

W is the group —C(O)— or a bond,

A5 and A6 are identical or different and are —C(O)—, —NH—, —O—, —S—, —C(O)—NH—, —NH—C(O)—, —O—C(O)—, —C(O)—O— or a bond, M is selected from one of the following groups

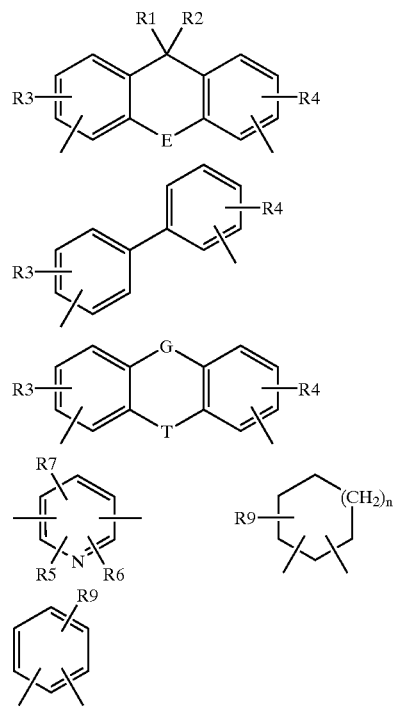

where

R1 and R2 are identical or different and are hydrogen, 1–4C-alkyl, 1–4C-alkyl which is wholly or partially substituted by fluorine, or hydroxyl, or R1 and R2 together, and including the carbon atom to which they are bonded, are —C(O)— or a 5- or 6-membered, optionally substituted cyclic hydrocarbon, R3 and R4 are identical or different and are hydrogen or one, two or three identical or different 1–4C-alkyl radicals, E is —CH₂—, —O— or a bond, G is —S—, —O— or —S(O)₂—, T is —CH₂—, —O— or a bond, R5 and R6 are identical or different and are hydrogen or 1–4C-alkyl, R7 is hydrogen, 1–4C-alkyl, phenyl or pyridyl, R9 is hydrogen or one, two or three identical or different 1–4C-alkyl radicals, n is 0, 1, 2 or 3, K1 is -B7-(C(O)) B9-X1, -B7-(C(O))$_m$-B9-Y1 or -B7-(C(O))$_m$-B9-Z1-B11-X1, K2 is -B8-(C(O))$_p$-B10-X2, -B8-(C(O))$_p$-B10-Y2 or -B8-(C(O))$_p$-B10-Z2-B12-X2, B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and selected from the following groups

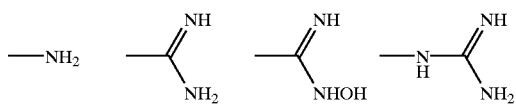

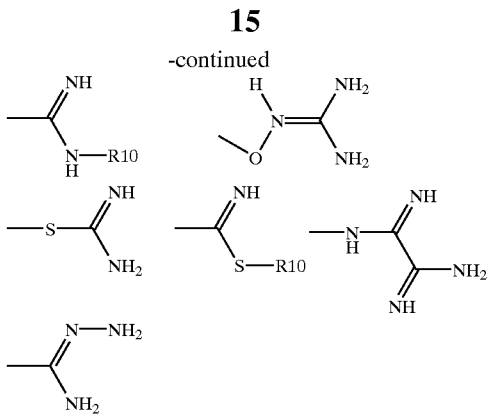

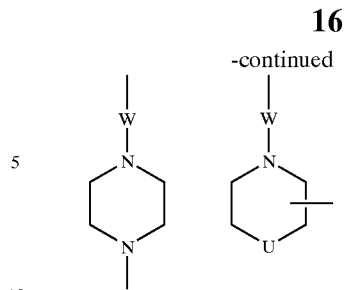

where

R10 is 1–4C-alkyl,

Y1 and Y2 are identical or different and are a 4–11C-heteroaryl or 2–7C-heterocycloalkyl radical which contains at least one ring nitrogen, Z1 and Z2 are identical or different and are 5–12C-arylene, 5–12C-heteroarylene, 3–8C-cycloalkylene or 3–8C-heterocycloalkylene, with each arylene, heteroarylene, cycloalkylene, heterocycloalkylene, heteroaryl or heterocycloalkyl additionally, for its part, being able to be substituted by one, two or three substituents selected from the group hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl, and in which 24 to 40 bonds must be present on the direct route between the terminal nitrogen atoms, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms, two carbonyl groups or one carbonyl group and one thiocarbonyl group.

Compounds of embodiment b which are to be emphasized are, on the one hand, those in which A1 and A2 are identical or different and are —C(O)—, —NH—, —O— (oxygen), —S— (sulfur), —S(O)₂—, —S(O)₂—NH—, —NH—S(O)₂—, —C(O).—NH—, —NH—C(O)—, —O—C(O)—, —C(O)—O— or a bond, A3 and A4 are identical or different and are —C(O)—, —C(S)—, —O—, —S—, —NH—, —O—C(O)—, —C(O)—O—, —C(O)—NH—, —NH—C(O)— or a bond, or are selected from the group

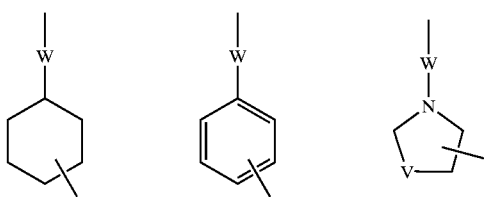

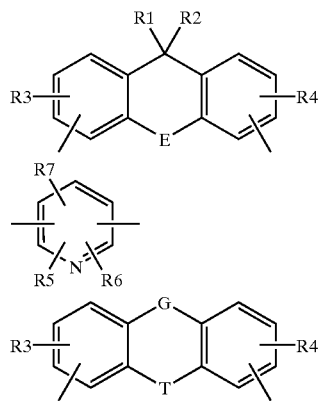

where

U is —O— (oxygen) or —CH₂— (methylene),

V is —O— (oxygen), —S— (sulfur) or —CH₂— (methylene), and

W is the group —C(O)— or a bond,

A5 and A6 are identical or different and are —C(O)—, —NH—, —O—, —S—, —C(O)—NH—, —NH—C(O)—, —O—C(O)—, —C(O)—O— or a bond, M is selected from one of the following groups where R1 and R2 are identical or different and are 1–4C-alkyl which is wholly or partially substituted by fluorine, or R1 and R2 together, and including the carbon atom to which they are bonded, are a 5- or 6-membered, optionally substituted cyclic hydrocarbon, R3 and R4 are identical or different and are hydrogen or one, two or three identical or different 1–4C-alkyl radicals, E is —CH₂—, —O— or a bond, G is —S(O)₂—, T is —CH₂—, —O— or a bond, R5 and R6 are identical or different and are hydrogen or 1–4C-alkyl, R7 is pyridyl, K1 is -B7-(C(O)) -B9-X1, -B7-(C(O))$_m$-B9-Y1 or -B7-(C(O))$_m$-B9-Z1-B11-X1, K2 is -B8-(C(O))$_p$-B10-X2, -B8-(C(O))$_p$-B10-Y2 or -B8-(C(O))$_p$-B10-Z2-B12-X2, B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

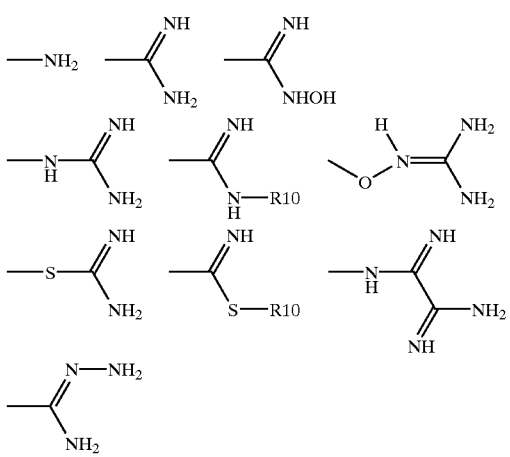

where

R10 is 1–4C-alkyl,

Y1 and Y2 are identical or different and are a 4–11C-heteroaryl or 2–7C-heterocycloalkyl radical which contains at least one ring nitrogen, Z1 and Z2 are identical or different and are 5–12C-arylene, 5–12C-heteroarylene, 3–8C-cycloalkylene or 3–8C-heterocycloalkylene, with each arylene, heteroarylene, cycloalkylene, heterocycloalkylene, heteroaryl or heterocycloalkyl additionally, for its part, being able to be substituted by one, two or three substituents selected from the group hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl, and in which 24 to 40 bonds must be present on the direct route between the terminal nitrogen atoms, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms, two carbonyl groups or one carbonyl group and one thiocarbonyl group.

On the other hand, compounds of embodiment b which are to be emphasized are those in which A1 and A2 are identical or different and are —C(O)—, —NH—, —O— (oxygen), —S— (sulfur), —S(O)₂—, —S(O)₂—NH—, —NH—S(O)₂—, —C(O)—NH—, —NH—C(O)—, —O—C(O)—, —C(O)—O— or a bond, A3 and A4 are identical or different and are —C(O)—, —C(S)—, —O—, —S—, —NH—, —O—C(O)—, —C(O)—O—, —C(O)—NH—, —NH—C(O)— or a bond, or are selected from the group

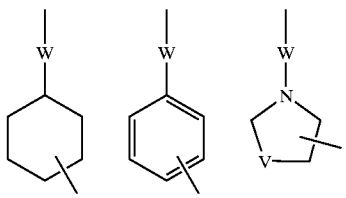

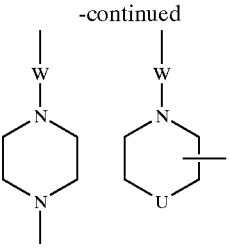

where

U is —O— (oxygen) or —CH₂— (methylene),

V is —O— (oxygen), —S— (sulfur) or —CH₂— (methylene), and

W is the group —C(O)— or a bond,

A5 and A6 are identical or different and are —C(O)—, —NH—, —O—, —S—, —C(O)—NH—, —NH—C(O)—, —O—C(O)—, —C(O)—O— or a bond, M is selected from one of the following groups

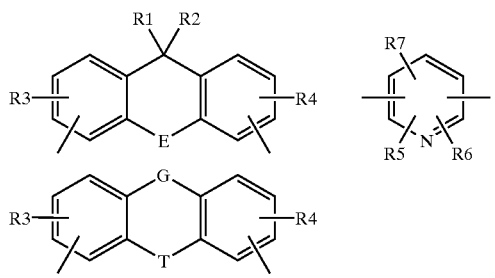

where

R1 and R2 are identical or different and are 1–4C-alkyl or together, and including the carbon atom to which they are bonded, are carbonyl, R3 and R4 are identical or different and are hydrogen or one, two or three identical or different 1–4C-alkyl radicals, E is —CH₂—, —O— or a bond, G is —O— (oxygen) or —S— (sulfur), T is —CH₂—, —O— or a bond, R5 and R6 are identical or different and are hydrogen or 1–4C-alkyl, R7 is hydrogen, 1–4C-alkyl or phenyl, K1 is -B7-(C(O))$_m$-B9-X1, -B7-(C(O))$_m$-B9-Y1 or -B7-(C(O))$_m$-B9-Z1-B11-X1, K2 is -B8-(C(O))$_p$-B10-X2, -B8-(C(O))$_p$-B10-Y2 or -B8-(C(O))$_p$-B10-Z2-B12-X2, B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

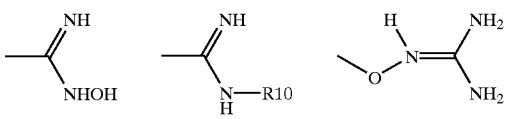

-continued

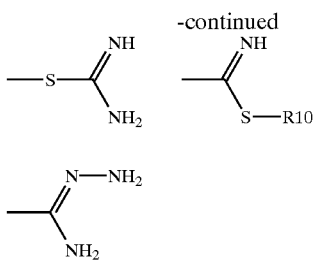

where
R10 is 1–4C-alkyl,
Y1 and Y2 are identical or different and are pyrrolidin-2-yl, imidazolidin-1-yl, imidazolidin-2-yl, imidazolidin-4-yl, pyridazin-4-yl, indol-3-yl or morpholin-2-yl,
Z1 and Z2 are identical or different and are 5–12C-arylene, 5–12C-heteroarylene, 3–8C-cycloalkylene or 3–8C-heterocycloalkylene,
with each arylene, heteroarylene, cycloalkylene, heterocycloalkylene, heteroaryl or heterocycloalkyl additionally, for its part, being able to be substituted by one, two or three substituents selected from the group hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl,
and in which 24 to 40 bonds must be present on the direct route between the terminal nitrogen atoms,
the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms, two carbonyl groups or one carbonyl group and one thiocarbonyl group.

Compounds of embodiment b which are furthermore to be emphasized are those in which
A1 and A2 are identical or different and are —C(O)—, —NH—, —O— (oxygen), —S— (sulfur)—, —S(O)$_2$—, —NH—S(O)$_2$—, —S(O)2—NH—, —NH—S(O)$_2$—, —C(O)—NH—, —NH—C(O)—, —O—C(O)—, —C(O)—O— or a bond,
A3 and A4 are identical or different and are —C(O)—, —C(S)—, —O—, —S—, —NH—, —O—C(O)—, —C(O)—O—, —C(O)—NH—, —NH—C(O)— or a bond, or are selected from the group

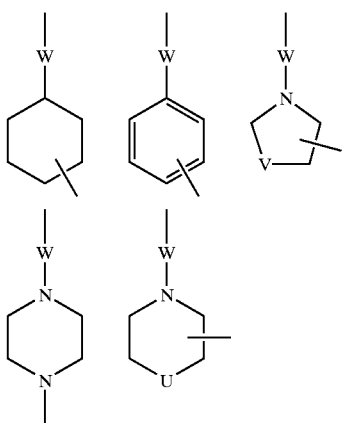

where
U is —O— (oxygen) or —CH$_2$— (methylene),
V is —O— (oxygen), —S— (sulfur) or —CH$_2$— (methylene), and
W is the group —C(O)— or a bond,
A5 and A6 are identical or different and are —C(O)—, —NH—, —O—, —S—, —C(O)—NH—, —NH—C(O)—, —O—C(O)—, —C(O)—O— or a bond,
M is selected from one of the following groups

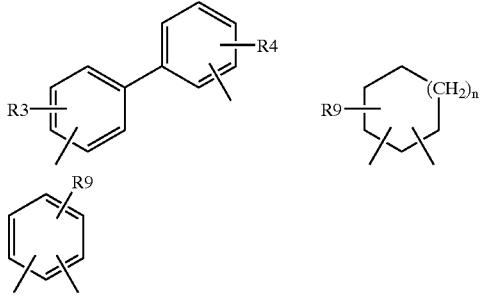

where
R3 and R4 are identical or different and are hydrogen or one, two or three identical or different 1–4C-alkyl radicals,
R9 is hydrogen or one, two or three identical or different 1–4C-alkyl radicals,
n is 0, 1, 2 or 3,
K1 is -B7-(C(O))$_m$-B9-X1, -B7-(C(O))$_m$-B9-Y1 or -B7-(C(O))$_m$-B9-Z1-B11-X1,
K2 is -B8-(C(O))$_p$-B10-X2, -B8-(C(O))$_p$-B10-Y2 or -B8-(C(O))$_p$-B10-Z2-B12-X2,
B1, B2, B3, B4, B5 and B6 are identical or different and are a bond or 1–4C-alkylene,
B7, B8, B9, B10, B11 and B12 are identical or different and are a bond or 1–3C-alkylene,
m is 0 or 1,
p is 0 or 1,
X1 and X2 are identical or different and are selected from the following groups

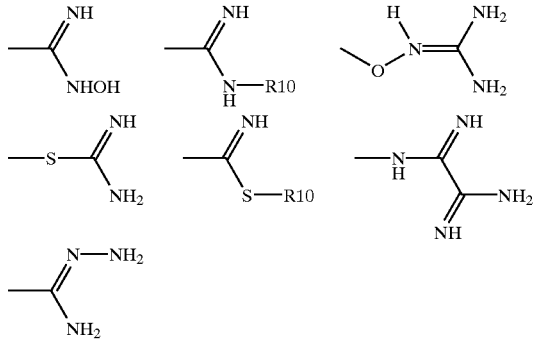

where
R10 is 1–4C-alkyl
Y1 and Y2 are identical or different and are pyrrolidin-2-yl, imidazolidin-1-yl, imidazolidin-2-yl, imidazolidin-4-yl, pyridazin-4-yl, indol-3-yl or morpholin-2-yl,
Z1 and Z2 are identical or different and are 5–12C-arylene, 5–12C-heteroarylene, 3–8C-cycloalkylene or 3–8C-heterocycloalkylene,
with each arylene, heteroarylene, cycloalkylene, heterocycloalkylene, heteroaryl or heterocycloalkyl additionally, for its part, being able to be substituted by one, two or three substituents selected from the group hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl,
and in which 24 to 40 bonds must be present on the direct route between the terminal nitrogen atoms,
the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms, two carbonyl groups or one carbonyl group and one thioncarbonyl group.

Compounds of embodiment b which are in particular to be emphasized are, on the one hand, those in which A1 and A2 are identical or different and are —C(O)—, —NH—, —O— (oxygen), —C(O)—NH—, —NH—C(O)—, —O—C(O)—, —C(O)—O— or a bond, A3 and A4 are identical or different and are —C(O)—, —O—, —NH—, —O—C(O)—, —C(O)—O—, —C(O)—NH—, —NH—C(O)— or a bond, or are selected from the group

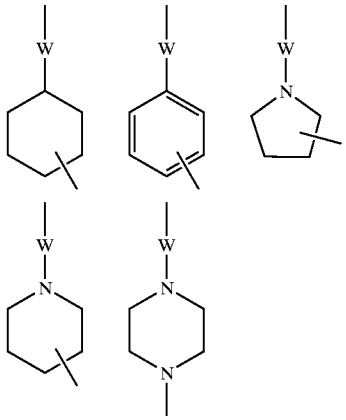

where

W is the group —C(O)— or a bond,

A5 and A6 are identical or different and are —C(O)—, —NH—, —O—, —C(O)—NH—, —NH—C(O)—, —O—C(O)—, —C(O)—O— or a bond, M is selected from one of the following groups

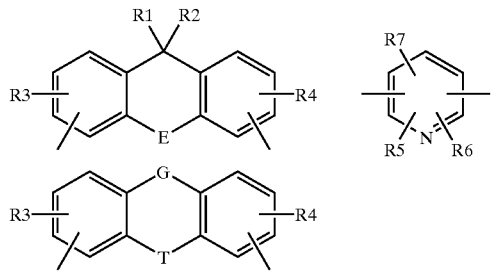

where

R1 and R2 are identical or different and are 1–4C-alkyl which is wholly or partially substituted by fluorine, or R1 and R2 together, and including the carbon atom to which they are bonded, are a 5- or 6-membered, optionally substituted cyclic hydrocarbon, R3 and R4 are identical or different and are hydrogen or one, two or three identical or different 1–4C-alkyl radicals, E is —CH$_2$—, —O— or a bond, G is —S(O)$_2$—, T is —CH$_2$—, —O— or a bond, R5 and R6 are identical or different and are hydrogen or 1–4C-alkyl, R7 is pyridyl, K1 is -B7-(C(O))$_m$-B9-X1, -B7-(C(O))$_m$-B9-Y1 or -B7-(C(O))$_m$-B9-Z1-B11-X1, K2 is -B8-(C(O))$_p$-B10-X2, -B8-(C(O))$_p$-B10-Y2 or -B8-(C(O))$_p$-B10-Z2-B12-X2, B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

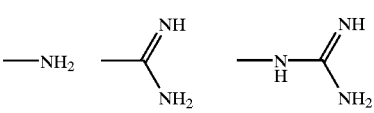

Y1 and Y2 are identical or different and are piperid-4-yl, piperid-3-yl, piperazin-1-yl, piperazin-2-yl, morpholin-2-yl, pyrrolidin-2-yl, pyrrolidin-3-yl, imidazolidin-1-yl, imidazolidin-2-yl, imidazolidin-4-yl, 2-imidazolin-3-yl, 2-imidazolin-2-yl, imidazol-1-yl, imidazol-2-yl, imidazol-4-yl, 5-methylimidazol-4-yl, pyrid-4-yl, pyrid-3-yl, pyridazin-4-yl, pyrimidin-5-yl, pyrimidin-4-yl, indol-3-yl, benzimidazol-4-yl or benzimidazol-5-yl, Z1 and Z2 are identical or different and are 1,4-phenylene, 1,3-phenylene, 1,4-naphthylene, 2,6-naphthylene, 1,4-cyclohexylene, 1,3-cyclohexylene, 1,3-cyclopentylene, 1,4-piperazinylene, 4,1-piperidinylene, 1,4-piperidinylene, 2,5-pyrrolidinylene, 4,2-imidazolidinylene, 2,5-furylene, 2,5-pyrrolylene, 4,2-pyridylene, 5,2-pyridylene, 6-methyl-5,2-pyridinylene, 2,5-indolylene, 2,6-indolylene, 3,5-indolylene, 3,6-indolylene, 3,5-indazolylene, 3,6-indazolylene, 2,6-quinolinylene, 2,5-benzofuranylene or 4,2-thiazolylene, and in which 24 to 40 bonds must be present on the direct route between the terminal nitrogen atoms, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms or two carbonyl groups.

Compounds of embodiment b which are in particular to be emphasized are, on the other hand, compounds of the formula I in which A1 and A2 are identical or different and are —C(O)—, —NH—, —O— (oxygen), —C(O)—NH—, —NH—C(O)—, —O—C(O)—, —C(O)—O— or a bond, A3 and A4 are identical or different and are —C(O)—, —O—, —NH—, —O—C(O)—, —C(O)—O—, —C(O)—NH—, —NH—C(O)— or a bond, or are selected from the group

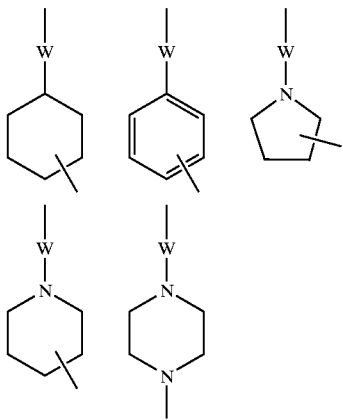

where

W is the group —C(O)— or a bond,

A5 and A6 are identical or different and are —C(O)—, —NH—, —O—, —C(O)—NH—, —NH—C(O)—, —O—C(O)—, —C(O)—O— or a bond, M is selected from one of the following groups

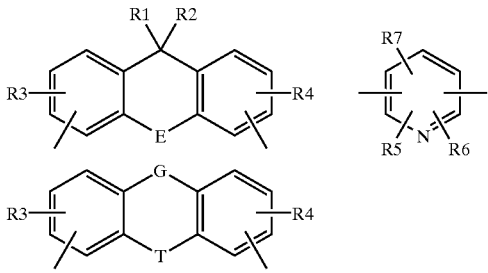

where

R1 and R2 are identical or different and are 1–4C-alkyl or together, and including the carbon atom to which they are bonded, are carbonyl, R3 and R4 are identical or different and are hydrogen or one, two or three identical or different 1–4C-alkyl radicals, E is —CH$_2$—, —O— or a bond, G is —O— (oxygen) or —S— (sulfur), T is —CH$_2$—, —O— or a bond, R5 and R6 are identical or different and are hydrogen or 1–4C-alkyl, R7 is hydrogen, 1–4C-alkyl or phenyl, K1 is -B7-(C(O))$_m$-B9-X1, -B7-(C(O))$_m$-B9 Y1 or -B7-(C(O))$_m$-B9-Z1-B11-X1, K2 is -B8-(C(O))$_p$-B10-X2, -B8-(C(O))$_p$-B10-Y2 or -B8-(C(O))$_p$-B10-Z2-B12-X2, B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

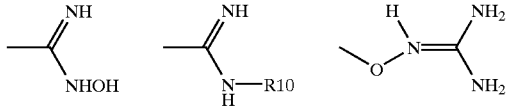

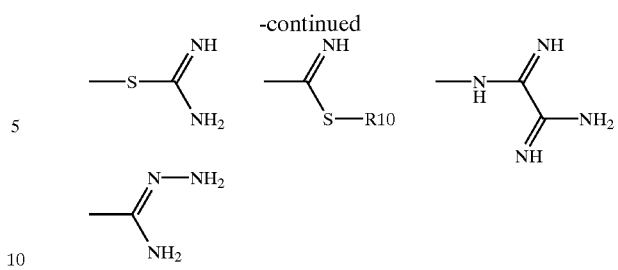

where

R10 is 1–4C-alkyl, Y1 and Y2 are identical or different and are pyrrolidin-2-yl, imidazolidin-1-yl, imidazolidin-2-yl, imidazolidin-4-yl, pyridazin-4-yl, indol-3-yl or morpholin-2-yl, Z1 and Z2 are identical or different and are 1,4-phenylene, 1,3-phenylene, 1,4-naphthylene, 2,6-naphthylene, 1,4-cyclohexylene, 1,3-cyclohexylene, 1,3-cyclopentylene, 1,4-piperazinylene, 4,1-piperidinylene, 1,4-piperidinylene, 2,5-pyrrolidinylene, 4,2-imidazolidinylene, 2,5-furylene, 2,5-pyrrolylene, 4,2-pyridylene, 5,2-pyridylene, 6-methyl-5,2-pyridinylene, 2,5-indolylene, 2,6-indolylene, 3,5-indolylene, 3,6-indolylene, 3,5-indazolylene, 3,6-indazolylene, 2,6-quinolinylene, 2,5-benzofuranylene or 4,2-thiazolylene, and in which 24 to 40 bonds must be present on the direct route between the terminal nitrogen atoms, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms or two carbonyl groups.

Compounds of embodiment b which are in particular to be emphasized are furthermore those in which A1 and A2 are identical or different and are —C(O)—, —NH—, —O— (oxygen), —C(O)—NH—, —NH—C(O)—, —O—C(O)—, —C(O)—O— or a bond, A3 and A4 are identical or different and are —C(O)—, —O—, —NH—, —O—C(O)—, —C(O)—O—, —C(O)—NH—, —NH—C(O)— or a bond, or are selected from the group

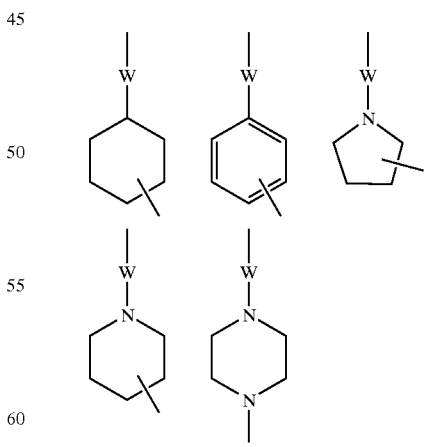

where

W is the group —C(O)— or a bond,

A5 and A6 are identical or different and are —C(O)—, —NH—, —O—, —C(O)—NH—, —NH—C(O)—, —O—C(O)—, —C(O)—O— or a bond, M is selected from one of the following groups

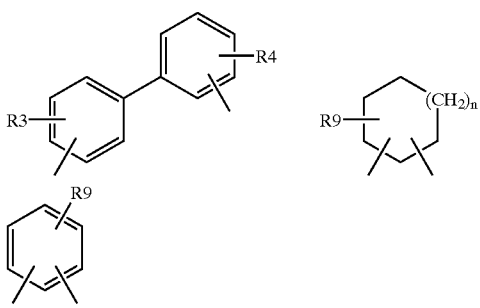

where

R3 and R4 are identical or different and are hydrogen or one, two or three identical or different 1–4C-alkyl radicals, R9 is hydrogen or one, two or three identical or different 1–4C-alkyl radicals, n is 0, 1, 2 or 3, K1 is -B7-(C(O))$_m$-B9-X1, -B7-(C(O))$_m$-B9-Y1 or -B7-(C(O))$_m$-B9-Z1-B11-X1, K2 is -B8-(C(O))$_p$-B10-X2, -B8-(C(O))$_p$-B10-Y2 or -B8-(C(O))$_p$-B10-Z2-B12-X2, B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

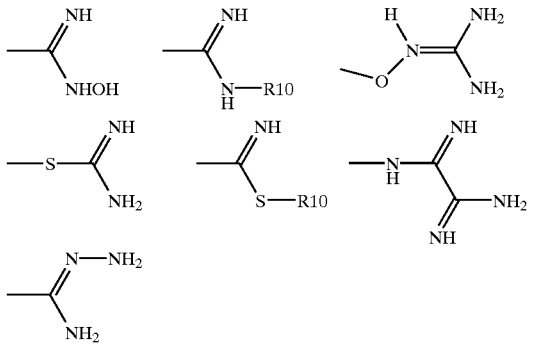

where

R10 is 1–4C-alkyl,

Y1 and Y2 are identical or different and are pyrrolidin-2-yl, imidazolidin-1-yl, imidazolidin-2-yl, imidazolidin-4-yl, pyridazin-4-yl, indol-3-yl or morpholin-2-yl, Z1 and Z2 are identical or different and are 1,4-phenylene, 1,3-phenylene, 1,4-naphthylene, 2,6-naphthylene, 1,4-cyclohexylene, 1,3-cyclohexylene, 1,3-cyclopentylene, 1,4-piperazinylene, 4,1-piperidinylene, 1,4-piperidinylene, 2,5-pyrrolidinylene, 4,2-imidazolidinylene, 2,5-furylene, 2,5-pyrrolylene, 4,2-pyridylene, 5,2-pyridylene, 6-methyl-5,2-pyridinylene, 2,5-indolylene, 2,6-indolylene, 3,5-indolylene, 3,6-indolylene, 3,5-indazolylene, 3,6-indazolylene, 2,6-quinolinylene, 2,5-benzofuranylene or 4,2-thiazolylene, and in which 24 to 40 bonds must be present on the direct route between the terminal nitrogen atoms, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms or two carbonyl groups.

Compounds of embodiment b which are in particular to be emphasized are, in addition, pyridine-2,6-dicarbobis[4-(3-aminomethylbenzoyl)-1-piperazide], pyridine-2,6-dicarbobis[4-(trans-4-aminomethylcyclohexanoyl)-1-piperazide], 2,6-dimethyl-4-phenylpyridine-3,5-dicarbobis[4-(3-aminomethylbenzoyl)-1-piperazide], pyridine-2,6-dicarbobis[4-(3-aminomethylbenzoylamino)-1-piperidide] and pyridine-2,6-dicarbobis[4-(4-aminomethylcyclohexylcarbonylamino)-1-piperidide], and also the salts of these compounds.

A further embodiment (embodiment c) of the compounds of the formula I is that in which A1 and A2 are identical or different and are —C(O)—, —NH—, —O— (oxygen), —S— (sulfur), —S(O)$_2$—, —S(O)$_2$—NH—, —NH—S(O)$_2$—, —C(O)—NH—, —NH—C(O)—, —O—C(O)—, —C(O)—O— or a bond, A3 and A4 are identical or different and are —C(O)—, —C(S)—, —O—, —S—, —NH—, —O—C(O)—, —C(O)—O—, —C(O)—NH—, —NH—C(O)— or a bond, or are selected from the group

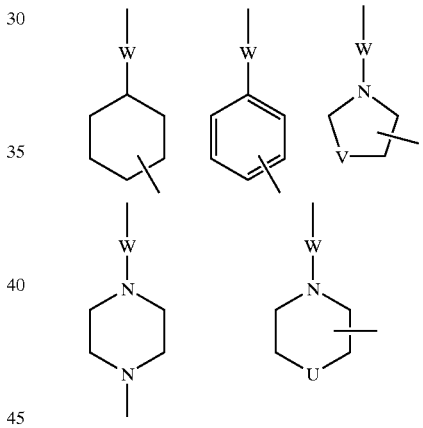

where

U is —O— (oxygen) or CH$_2$— (methylene),

V is —O— (oxygen), —S— (sulfur) or —CH$_2$— (methylene), and

W is the group —C(O)— or a bond,

A5 and A6 are identical or different and are —C(O)—, —NH—, —O—, —S—, —C(O)—NH—, —NH—C(O)—, —O—C(O)—, —C(O)—O— or a bond, M is selected from one of the following groups

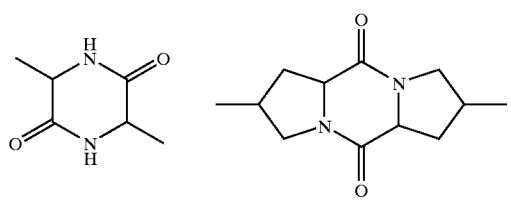

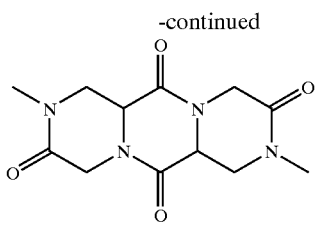

K1 is -B7-(C(O))$_m$-B9-X1, -B7-(C(O))$_m$-B9-Y1 or -B7-(C(O))$_m$-B9-Z1 B11 X1,

K2 is -B8-(C(O))$_p$-B10-X2, -B8-(C(O))$_p$-B10-Y2 or -B8-(C(O))$_p$-B10-Z2-B12-X2,

B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

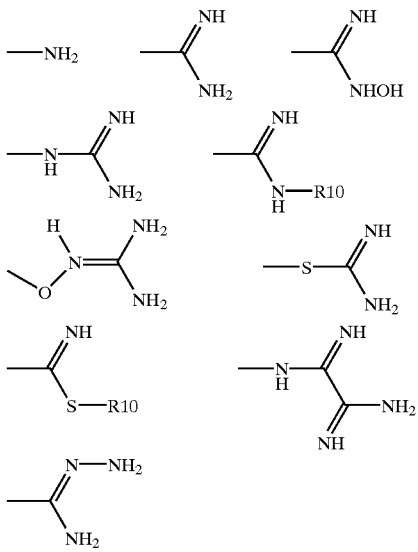

where

R10 is 1–4C-alkyl,

Y1 and Y2 are identical or different and are a 4–4C-heteroaryl or 2–7C-heterocycloalkyl radical which contains at least one ring nitrogen, Z1 and Z2 are identical or different and are 5–12C-arylene, 5–12C-heteroarylene, 3–8C-cycloalkylene or 3–8C-heterocycloalkylene, with each arylene, heteroarylene, cycloalkylene, heterocycloalkylene, heteroaryl or heterocycloalkyl additionally, for its part, being able to be substituted by one, two or three substituents selected from the group hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl, and in which 24 to 40 bonds must be present on the direct route between the terminal nitrogen atoms, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms, two carbonyl groups or one carbonyl group and one thiocarbonyl group.

Compounds of embodiment c which are to be emphasized are those in which

A1 and A2 are identical or different and are —C(O)—, —NH—, —O— (oxygen), —S— (sulfur), —S(O)$_2$—, —S(O)$_2$—NH—, —NH—S(O)$_2$—, —C(O)—NH—, —NH—C(O)—, —O—C(O)—, —C(O)—O— or a bond, A3 and A4 are identical or different and are —C(O)—, —C(S)—, —O—, —S—, —NH—, —O—C(O)—, —C(O)—O—, —C(O)—NH—, —NH—C(O)— or a bond, or are selected from the group

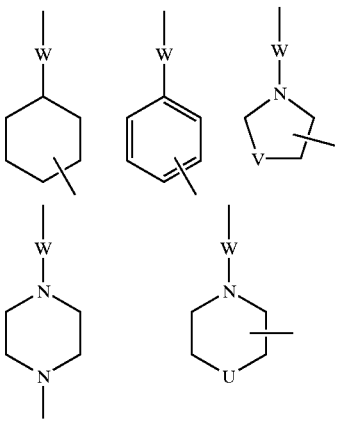

where

U is —O— (oxygen) or —CH$_2$— (methylene),

V is —O— (oxygen), —S— (sulfur) or —CH$_2$— (methylene), and

W is the group —C(O)— or a bond,

A5 and A6 are identical or different and are —C(O)—, —NH—, —O—, —S—, —C(O)—NH—, —NH—C(O)—, —O—C(O)—, —C(O)—O— or a bond, M is selected from one of the following groups

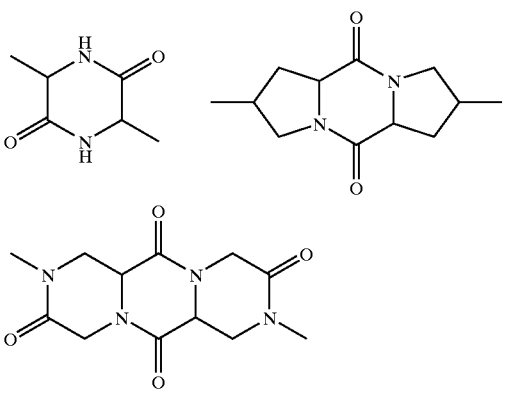

where

K1 is -B7-(C(O))$_m$-B9-X1, -B7-(C(O))$_m$-B9-Y1 or -B7-(C(O))$_m$-B9-Z1-B11-X1,

K2 is -B8-(C(O))$_p$-B10-X2, -B8-(C(O))$_p$-B10-Y2 or -B8-(C(O))$_p$-B10-Z2-B12-X2,

B1, B2, B3, B4, B5 and B6 are identical or different and are a bond or 1–4C-alkylene, B7, B8, B9, B10, B11 and B12 are identical or different and are a bond or 1-3C-alkylene, m is 0 or 1, p is 0 or 1, X1 and X2 are identical or different and are selected from the following groups

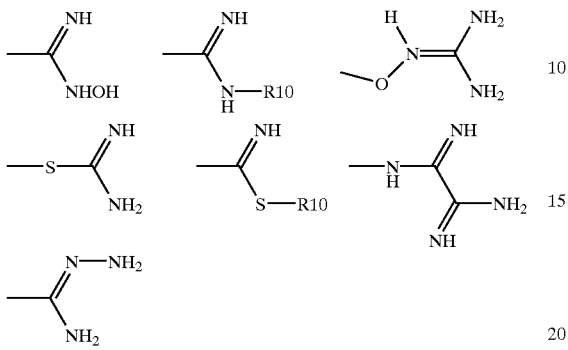

where

R10 is 1–4C-alkyl,

Y1 and Y2 are identical or different and are pyrrolidin-2-yl, imidazolidin-1-yl, imidazolidin-2-yl, imidazolidin-4-yl, pyridazin-4-yl, indol-3-yl or morpholin-2-yl, Z1 and Z2 are identical or different and are 5–12C-arylene, 5–12C-heteroarylene, 3–8C-cycloalkylene or 3–8C-heterocycloalkylene, with each arylene, heteroarylene, cycloalkylene, heterocycloalkylene, heteroaryl or heterocycloalkyl additionally, for its part, being able to be substituted by one, two or three substituents selected from the group hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl, and in which 24 to 40 bonds must be present on the direct route between the terminal nitrogen atoms, the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms, two carbonyl groups or one carbonyl group and one thiocarbonyl group.

Compounds of embodiment c which are in particular to be emphasized are those in which A1 and A2 are identical or different and are —C(O)—, —NH—, —O— (oxygen), —C(O)—NH—, —NH—C(O)—, —O—C(O)—, —C(O)—O— or a bond, A3 and A4 are identical or different and are —C(O)—, —O—, —NH—, —O—C(O)—, —C(O)—O—, —C(O)—NH—, —NH—C(O)— or a bond, or are selected from the group

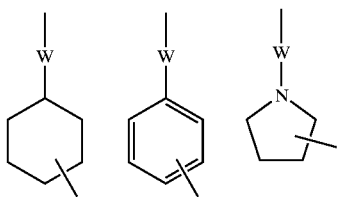

-continued

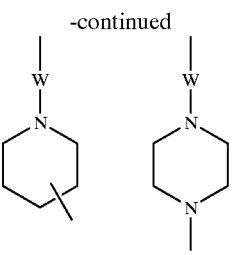

where

W is the group —C(O)— or a bond,

A5 and A6 are identical or different and are —C(O)—, —NH—, —O—, —C(O)—NH—, —NH—C(O)—, —O—C(O)—, —C(O)—O— or a bond, M is selected from one of the following groups

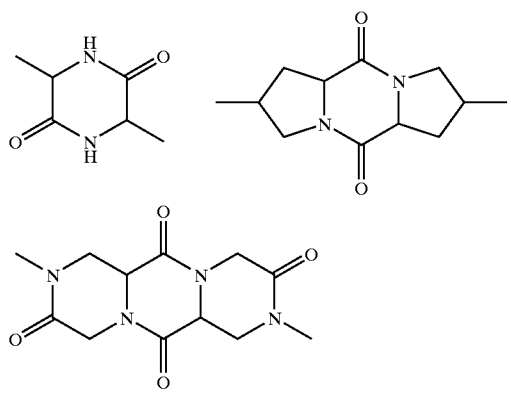

K1 is -B7-(C(O))$_m$-B9-X1, -B7-(C(O))$_m$-B9-Y1 or -B7-(C ))$_m$-B9-Z1-B11-X1,

K2 is -B8-(C(O))$_p$-B10-X2, -B8-(C(O))$_p$-B10-Y2 or -B8-(C(O))$_p$-B10-Z2-B12-X2,

B1, B2, B3, B4, B5 and B6 are identical or different and are a bond or 1–4C-alkylene, B7, B8, B9, B10, B11 and B12 are identical or different and are a bond or 1–3C-alkylene, m is 0 or 1, p is 0 or 1, X1 and X2 are identical or different and are selected from the following groups

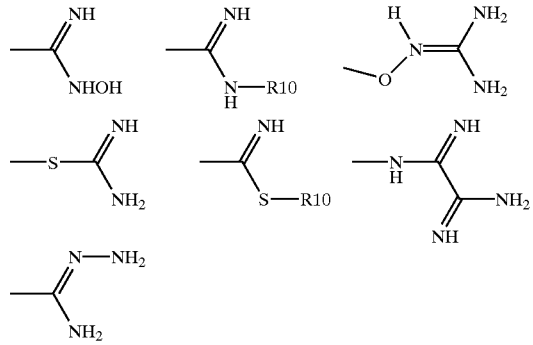

where

R10 is 1–4C-alkyl,

Y1 and Y2 are identical or different and are pyrrolidin-2-yl, imidazolidin-1-yl, imidazolidin-2-yl, imidazolidin-4-yl, pyridazin-4-yl, indol-3-yl or morpholin-2-yl, Z1 and Z2 are identical or different and are 1,4-phenylene, 1,3-phenylene, 1,4-naphthylene, 2,6-naphthylene, 1,4- cyclohexylene, 1,3-cyclohexylene, 1,3-cyclopentylene, 1,4-piperazinylene, 4,1-piperidinylene, 1,4-piperidinylene, 2,5-pyrrolidinylene, 4,2-imidazolidinylene, 2,5-furylene, 2,5-pyrrolylene, 4,2-pyridylene, 5,2-pyridylene, 6-methyl-5,2-pyridinylene, 2,5-indolylene, 2,6-indolylene, 3,5-indolylene, 3,6-indolylene, 3,5-indazolylene, 3,6-indazolylene, 2,6-quinolinylene, 2,5-benzofuranylene or 4,2-thiazolylene,
and in which 24 to 40 bonds must be present on the direct route between the terminal nitrogen atoms,
the salts of these compounds, and also the N-oxides of the heteroaryls, heterocycloalkyls, heteroarylenes and heterocycloalkylenes which contain a nitrogen atom, and their salts, with all those compounds being excluded in which one or more of the variables B1, B2, B3, B4, B5, B6, B7, B8, B9, B10, B11 or B12 assume the meaning of a bond, with this thereby resulting in the direct linkage of two heteroatoms or two carbonyl groups.

The compounds of the formula I are composed of a large number of divalent building blocks (M, A1, A2, A3, A4, A5, A6, B1, B2, B3, B4, B5, B6, B7, B8, B9, B10, B11, B12, Z1 and Z2). In principle, they can be synthesized starting from any one of these building blocks. In the case of compounds of the formula I which are constructed to a large extent symmetrically, preference is given to starting the synthesis with the central building block M; by contrast, it can be advantageous to synthesize compounds of the formula I which are predominantly asymmetrical starting with one of the end groups K1 or K2.

In this connection, the building blocks are always linked together in accordance with the same pattern, which is known per se to the skilled person.

The skilled person knows that the compounds of the formula I can be synthesized building block by building block; alternatively, relatively large fragments, consisting of several individual building blocks, can first of all be constructed, with these fragments then being assembled into the whole molecule.

Amino [—NH—], ether [—O—], thioether [—S—], keto [—C(O)—], thioketo [—C(S)—], sulfonyl [—S(O)$_2$—], ester [—O—C(O)—, —C(O)—O—], amide [—C(O)—NH—, —NH—C(O)—], sulfonamide [—SO$_2$—NH—, —NH—SO$_2$—], carbamate [—NH—C(O)—O—, —O—C(O)—NH—], carbamide (—NH—C(O)—NH—) or carbonate [—O—C(O)—O—] bridges occur in the compounds of the formula I as a result of the meanings which the individual building blocks of the compounds of the formula I can assume.

The manner in which such bridges are prepared is known per se to the skilled person, and suitable methods, and starting compounds for preparing them, are described, for example, in March, Advanced Organic Chemistry, Reactions, Mechanisms and Structure, Third Edition, 1985, John Wiley & Sons.

For example, ether and thioether bridges can be prepared by the method of Williamson.

Keto or thioketo bridges can, for example, be introduced as components of larger building blocks, such as 1,3-dichloroacetone.

Sulfonyl bridges can be obtained, for example, by oxidizing thioether bridges.

A large number of methods are known for synthesizing ester bridges. Mention may be made here, by way of example, of the reaction of acids with alcohols, preferably using H$_2$SO$_4$ or p-toluenesulfonic acid as catalyst; or with the addition of a water-extracting agent, such as a molecular sieve or a carbodiimide. The reaction of acid chlorides with alcohols may also be mentioned at this point.

There is also a large number of known methods for preparing amide bridges. The reaction of acid chlorides with primary or secondary amines may be mentioned here as an example. In addition, reference may also be made to all the methods which have been developed for peptide chemistry. Correspondingly, sulfonamide bridges can be synthesized from sulfonyl chlorides and primary or secondary amines.

Carbamate bridges can be prepared, for example, by reacting chlorocarbonic esters with amines. The chlorocarbonic esters can, for their part, be synthesized from alcohols and phosgene.

The addition of alcohols to isocyanates constitutes another variant for synthesizing carbamate bridges.

In a similar way to carbamate bridges, carbonate bridges can be prepared from chlorocarbonic esters by reacting them with alcohols (instead of amines).

Carbamide bridges can be prepared, for example, by reacting isocyanates with amines.

It is also possible to convert compounds of the formula I by derivatization into other compounds of the formula I. Thus, for example, compounds of the formula I which have a nitrogen-containing heteroaryl or heterocycloalkyl building block can be converted by oxidation into the corresponding N-oxides.

The N oxidation is effected in a manner with which the skilled person is also familiar, for example using hydrogen peroxide in methanol or m-chloroperoxybenzoic acid in dichloromethane at room temperature. The skilled person is familiar, on the basis of his specialist knowledge, with the detailed reaction conditions which are required for carrying out the method.

It is furthermore known to a person skilled in the art that, if a starting material or intermediate contains a plurality of reactive centers, it may be required to protect one or more reactive centers temporarily by protective groups so that a reaction can take place selectively at the desired reaction center. A detailed description of how a large number of proven protective groups are used is given, for example, in T. W. Greene, Protective Groups in Organic Synthesis, John Wiley & Sons, 1991.

The substances according to the invention are isolated and purified in a manner known per se, for example by the solvent being distilled off in vacuo and the resulting residue being recrystallized from a suitable solvent or being subjected to one of the customary purification methods such as column chromatography on a suitable support material.

Salts are obtained by dissolving the free compound in a suitable solvent, for example in a chlorinated hydrocarbon, such as methylene chloride or chloroform, or a low molecular weight aliphatic alcohol (ethanol, isopropanol), which contains the desired acid or base, or to which the desired acid or base is subsequently added. The salts are isolated by filtering, reprecipitation or precipitation with a substance which does not dissolve the addition salt, or by evaporating off the solvent. Resulting salts can be converted, by alkalizing or acidifying, into the free compounds, which can be converted into salts once again. In this way, salts which are not tolerated pharmacologically can be converted into salts which are tolerated pharmacologically.

The preparation of compounds of the formula I may be demonstrated, by way of example, with the aid of the following Examples 1 to 12 and FIGS. 1 to 12. Other compounds of the formula I can be prepared analogously or using the methods which are cited above and which are known per se to the skilled person.

FIGS. 1, 2, 3, 4, 5, 6, 7, 8, 9, 10, 11 and 12 show formula schemes for preparing bifunctional inhibitors according to the invention.

EXAMPLES

Example 1

End Product

Pyridine-2,6-dicarbobis[4-(3-aminomethylbenzoyl)-1-piperazide] (1) (cf. FIG. 1)

1.3 ml of a 4.8 N solution of HCl in dioxane (6.2 mmol) are added dropwise to a solution of 600 mg (780 μmol) of pyridine-2,6-dicarbobis[4-(3-butyloxycarbonylaminomethylbenzoyl)-1-piperazide] in 7 ml of dioxane. 10 ml of methanol are added to the thick suspension and the mixture is stirred for 2.5 hours. It is then concentrated and the residue is taken up in 25 ml of water and the solution is adjusted to pH=11 (NaOH). The solution is then extracted with 3×20 ml of dichloromethane, and the combined organic phases are dried over $MgSO_4$ and concentrated. The product is dissolved in 2 ml of dioxane, with 0.5 ml of a 4.8 N solution of HCl in dioxane (2.4 mmol) then being added; the suspension is diluted with 15 ml of diethyl ether. The title compound is isolated as hydrochloride having a m.p. of >260° C.

Starting Compounds

Pyridine-2,6-dicarbobis[4-(3-tert-butyloxycarbonylaminomethylbenzoyl)-1-piperazide] (2)

1.36 ml (9.7 mmol) of triethylamine, 610 mg (2.42 mmol) of 3-tert-butyloxycarbonylaminomethylbenzoic acid, 330 mg (2.42 mmol) of 1-hydroxybenzotriazole and 460 mg (2.42 mmol) of N-(3-dimethylaminopropyl)-N'-ethyl-carbodiimide hydrochloride (EDC×HCl) are added, one after the other, to a suspension of 500 mg (1.21 mmol) of pyridine-2,6-dicarbobispiperazide trihydrochloride in 15 ml of DMF. After 75 min., the reaction mixture is extensively concentrated, after which 20 ml of water are added to the residue and the resulting solution is adjusted to pH=11 (NaOH). It is then extracted with 3×20 ml of dichloromethane, after which the combined organic phases are dried over $MgSO_4$ and concentrated, and the crude product is chromatographed through silica gel (ethyl acetate/methanol=10:1). The eluate is concentrated and the residue is stirred thoroughly in diethyl ether. 700 mg (75%) of the title compound having a m.p. of 195° C. (frothing at 110° C.) are obtained.

Pyridine-2,6-dicarbobispiperazide (3)

6.8 ml of a 4.8 N solution of HCl in dioxane (16.2 mmol) are added dropwise to a suspension of 2.05 g (4.07 mmol) of pyridine-2,6-dicarbobis-4-tert-butyloxycarbonylpiperazide in 20 ml of dioxane. The suspension is diluted with 10 ml of methanol and the mixture is stirred at room temperature overnight. The solvent is extensively concentrated, after which the suspension is thoroughly stirred with diethyl ether and filtered under a protective gas atmosphere. 1.7 g (100%) of the trihydrochloride of the title compound are obtained. m.p. >260° C.

Pyridine-2,6-dicarbobis-4-tert-butyloxycarbonylpiperazide (4)

1.0 g (5.0 mmol) of 2,6-pyridinedicarbonyl dichloride in 10 ml of dioxane is added dropwise to a solution of 1.88 g (10.1 mmol) of tert-butyl piperazine-N-carboxylate in 0.82 ml (10.1 mmol) of pyridine, 3.5 ml (25.2 mmol) of triethylamine and 10 ml of dioxane. The mixture is stirred at room temperature overnight, after which the precipitate is filtered off and the mother liquor is concentrated to dryness. The residue is extracted with 3×30 ml of dichloromethane from 30 ml of water. The organic phase, which has been dried over $MgSO_4$, is concentrated and the residue is crystallized from diethyl ether. 2.16 g (90%) of the title compound having a m.p. of 183–186° C. are obtained.

Example 2

End Products

Figure 2:
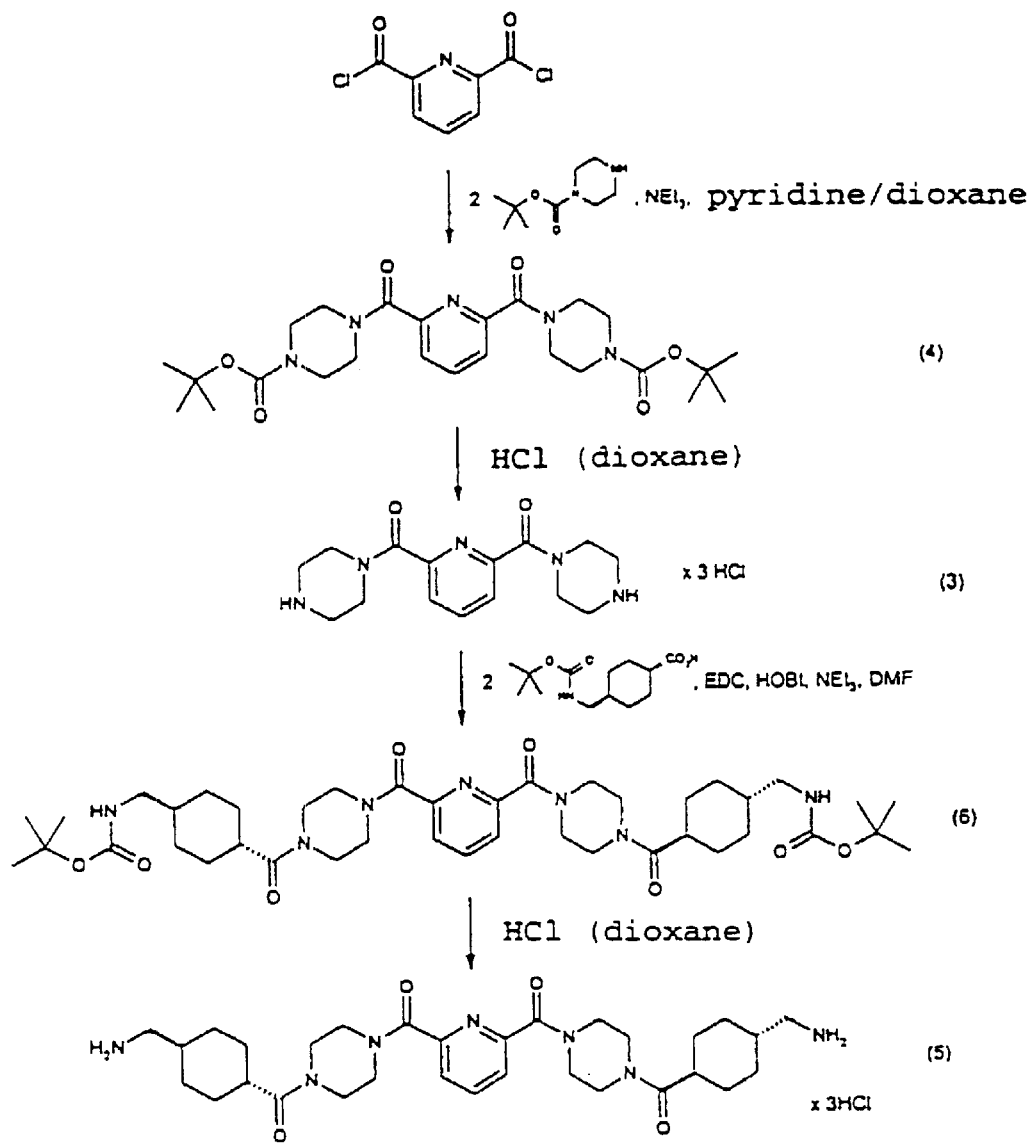

Pyridine-2,6-dicarbobis[4-(trans-4-aminomethylcyclohexanoyl)-1-piperazide] (5) (cf. FIG. 2)

1.06 ml of a 4.6 N solution of HCl in dioxane (5.1 mmol) are added dropwise to a solution of 500 mg (640 μmol) of pyridine-2,6-dicarbobis[4-(trans-4-tert-butyloxycarbonylaminomethylcyclohexylcarbonyl)-1-piperazide] in 10 ml of dioxane. 20 ml of methanol are added to the thick suspension and the whole is stirred at 40° C. for 4 hours. The mixture is concentrated; the residue is then coevaporated with 2×20 ml of toluene and crystallized from diethyl ether. The title compound is isolated as the dihydrochloride having a m.p. of 170° C. (frothing).

Example 3

Figure 3:
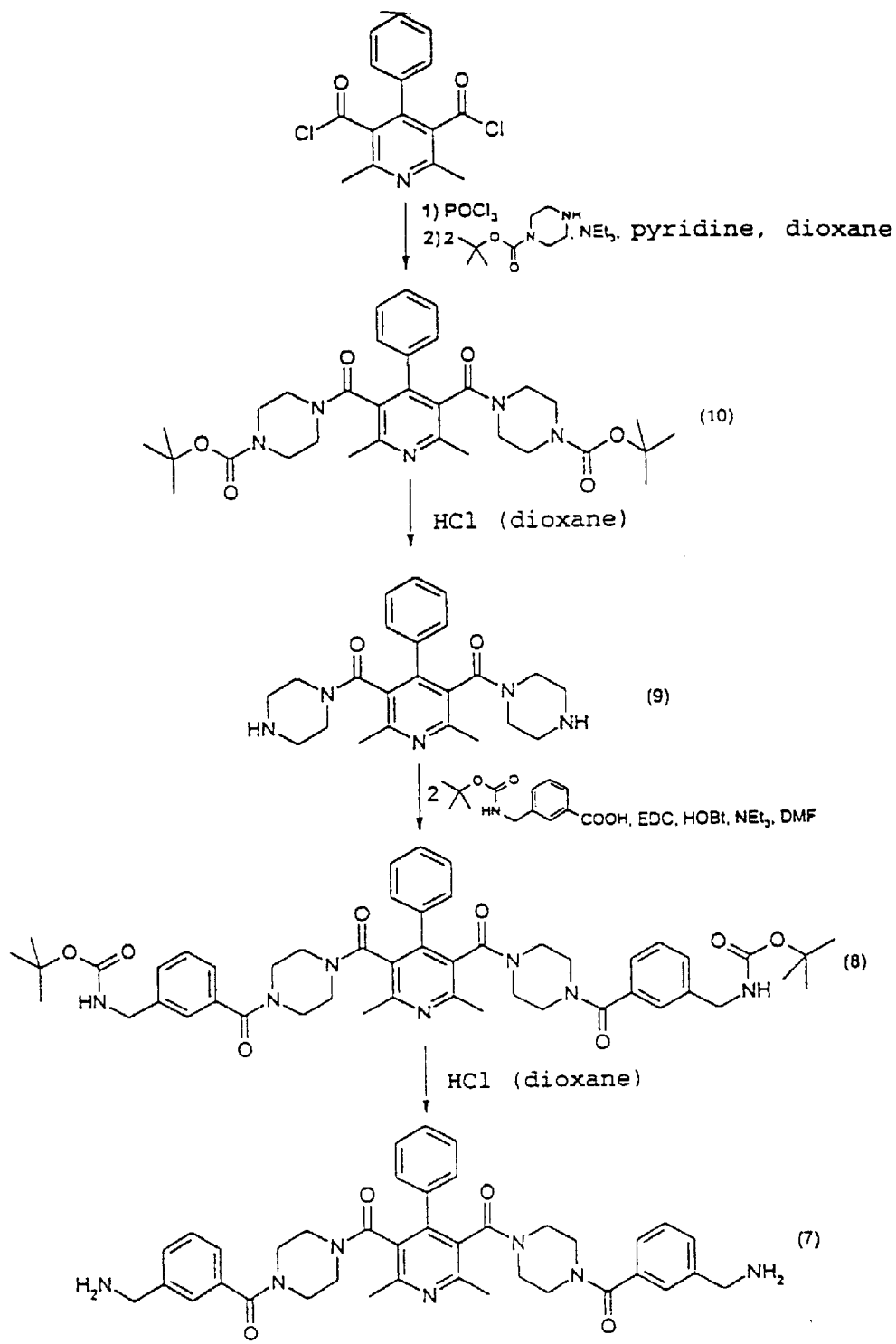

2,6-Dimethyl-4-phenylpyridine-3,5-dicarbobis[4-(3-aminomethylbenzoyl)-1-piperazide] (7) (cf. FIG. 3)

522 μl of a 4.6 N solution of HCl in dioxane (2.4 mmol) are added to a solution of 350 mg (0.4 mmol) of 2,6-dimethyl-4-phenylpyridine-3,5-dicarbobis[4-(3-tert-butyloxycarbonylaminomethylbenzoyl)-1-piperazide] in 5 ml of dioxane and 5 ml of methanol. After the mixture has been stirred overnight at room temperature, a further 200 μl (0.9 mmol) of HCl in dioxane are added and the reaction mixture is heated at 40° C. for 5 hours. The mixture is concentrated, and the residue is stirred up with 5 ml of dioxane and 2 ml of diethyl ether, and the title compound is isolated as dihydrochloride having a m.p. of 250° C. (sintering at 223° C.).

Starting Compounds

Pyridine-2,6-dicarbobis[4-(trans-4-tert-butyloxycarbonylaminomethylcyclohexylcarbonyl)-1-piperazide] (6)

1.36 ml (9.7 mmol) of triethylamine, 620 mg (2.42 mmol) of trans-4-tert-butyloxycarbonylaminomethylcyclohexanecarboxylic acid, 330 mg (2.42 mmol) of 1-hydroxybenzotriazole and 460 mg (2.42 mmol) of N-(3-dimethylaminopropyl)-N'-ethylcarbodiimide hydrochloride (EDC×HCl) are added, one after the other, to a suspension of 500 mg (1.21 mmol) of pyridine-2,6-dicarbobispiperazide trihydrochloride in 15 ml of DMF. After 45 min., the reaction mixture is extensively concentrated, after which 20 ml of water are added to the residue and the resulting solution is adjusted to pH=12 (NaOH). It is then extracted with 3×20 ml of dichloromethane, after which the combined organic phases are dried over $MgSO_4$ and concentrated, and the crude product is chromatographed through silica gel (ethyl acetate/methanol/ammonia=10:1:0.5). The eluate is concentrated and the residue is stirred thoroughly in diisopropyl ether. 620 mg (65%) of the title compound, having a m.p. of 200–202° C., are obtained.

2,6-Dimethyl-4-phenylpyridine-3,5-dicarbobis[4-(3-tert-butyloxycarbonylaminomethylbenzoyl)-1-piperazide] (8)

500 µl (4.2 mmol) of triethylamine, 280 mg (1.1 mmol) of 3-tert-butyloxycarbonylaminomethylbenzoic acid, 280 mg (1.1 mmol) of 1-hydroxybenzotriazole and 280 mg (2.1 mmol) of N-(3-dimethylaminopropyl)-N'-ethyl-carbodiimide hydrochloride (EDCxHCl) are added, one after the other, to a suspension of 220 mg (0.53 mmol) of 2,6-dimethyl-4-phenylpyridine-3,5-dicarbobispiperazide in 10 ml of DMF. After 4 hours, the reaction mixture is extensively concentrated after which 30 ml of water are added to the residue and the resulting solution is adjusted to pH=12 (NaOH). It is then extracted with a total of 70 ml of dichloromethane, after which the combined organic phases are dried over MgSO$_4$ and concentrated, and the crude product is chromatographed through silica gel (ethyl acetate/methanol=10:1). The eluate is concentrated and the residue is stirred thoroughly in diisopropyl ether. 446 mg (96%) of the title compound, having a m.p. of 113° C., are obtained.

2,6-Dimethyl-4-phenylpyridine-3,5-dicarbobispiperazide (9)

12.6 ml of a 4.6 N solution of HCl in dioxane (57.6 mmol) are added dropwise to a suspension of 15 5.87 g (9.6 mmol) of 2,6-dimethyl-4-phenylpyridine-3,5-dicarbobis-4-tert-butyloxycarbonylpiperazide in 20 ml of dioxane and 10 ml of methanol. The mixture is stirred at room temperature for 5 hours. The solvent is concentrated and the residue is thoroughly stirred with 30 ml of diethyl ether and 70 ml of methanol. 4.35 g (94%) of the dihydrochloride of the title compound, having a m.p. of >250° C., are obtained.

2,6-Dimethyl-4-phenylpyridine-3,5-dicarbobis-4-tert-butyloxycarbonylpiperazide (10)

13.0 g (mmol) of dipotassium 2,6-dimethyl-4-phenylpyridine-3,5-dicarboxylate are boiled, at 100° C. for 5 hours and under a nitrogen atmosphere, in 80 ml of phosphorus oxychloride. The phosphorus oxychloride is distilled off in vacuo and the residue is coevaporated with 3×50 ml of toluene. A suspension of a crude acid chloride in 200 ml of dioxane is added dropwise, while controlling the temperature (<30° C.), to a solution of 12.8 g (66 mmol) of tert-butyl piperazine-N-carboxylate, 5.3 ml (66 mmol) of pyridine and 46 ml (450 mmol) of triethylamine in 100 ml of dioxane. After one hour, the inorganic salts are filtered off and the filtrate is concentrated. The residue is extracted from 100 ml of water using 3×70 ml of ethyl acetate. The combined organic phases, which have been dried over MgSO$_4$, are concentrated and the residue is chromatographed through silica gel (ethyl acetate/methanol=10:1). 7.13 g (35%) of the title compound are obtained as a yellowish oil.

Example 4

End Product

Figure 4:
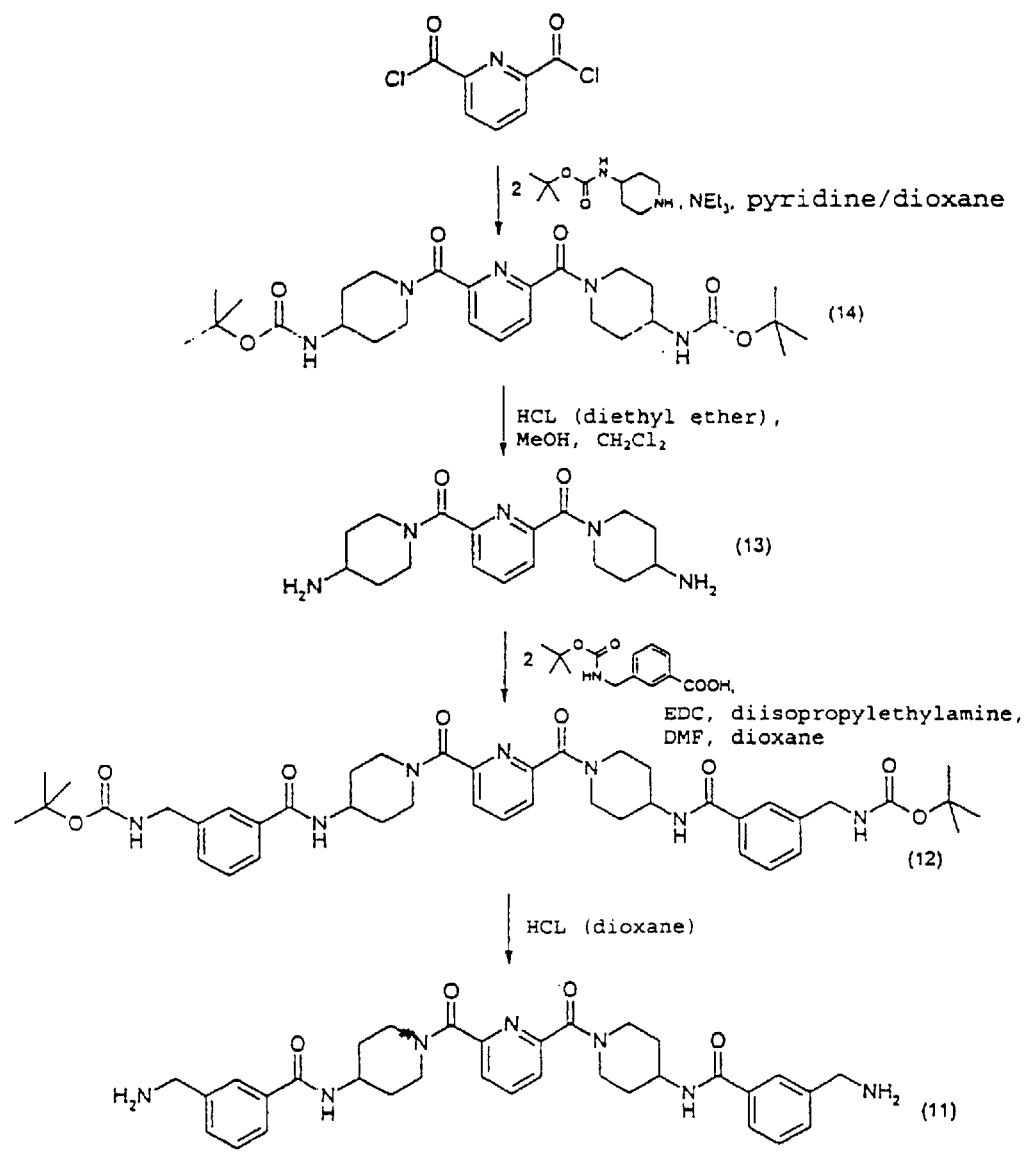

Pyridine-2,6-dicarbobis[4-(3-aminomethylbenzoylamino)-1-piperidide] (11) (cf. FIG. 4)

275 µl of a 4 N solution of HCl in dioxane (1.1 mmol) are added dropwise to a solution of 220 mg (275 µmol) of pyridine-2,6-dicarbobis[4-(3-tert-butyloxycarbonylaminomethylbenzoylamino)-1-piperidide] in 5 ml of dioxane. 3 ml of methanol are added to the thick suspension and the whole is stirred for 12 hours. The mixture is concentrated and the residue is coevaporated with 2×20 ml of toluene and crystallized. 130 mg of the title compound, having a m.p. of 230° C. (frothing), are obtained.

Starting Compounds

Pyridine-2,6-dicarbobis[4-(3-tert-butyloxycarbonylaminomethylbenzoylamino)-1-piperidide] (12)

342 mg (1.36 mmol) of 3-tert-butyloxycarbonylaminomethylbenzoic acid, 240 µl (1.36 mmol) of Hunig's base, 30 mg of diaminopyridine and 260 mg (1.36 mmol) of N-(3-dimethylaminopropyl)-N'-ethylcarbodiimide hydrochloride (EDCxHCl) are added, one after the other, to a suspension of 250 mg (0.62 mmol) of pyridine-2,6-dicarbobis(4-amino-1-piperidide) dihydrochloride in 2.5 ml of DMF and 2.5 ml of dioxane. After having been stirred at room temperature for 12 hours, the reaction mixture is concentrated, after which 10 ml of water are added to the residue and the resulting solution is adjusted to pH=3 (0.1 N HCl). It is then extracted with 3×20 ml of dichloromethane, after which the combined organic phases are dried over MgSO$_4$ and concentrated, and the crude product is chromatographed through silica gel (dichloromethane/methanol=19:1). The product-containing eluate is concentrated and the residue is thoroughly stirred in diethyl ether. 280 mg (57%) of the title compound, having a m.p. of 140° C. (frothing, sintering from 120° C. onward) are obtained.

Pyridine-2,6-dicarbobis(4-amino-1-piperidide) (13)

12 ml of a 6 N solution of HCl in diethyl ether (72 mmol) are added dropwise to a solution of 2.0 g (3.76 mmol) of pyridine-2,6-dicarbobis(4-tert-butyloxycarbonylamino-1-piperidide) in 10 ml of diethyl ether, 30 ml of methanol and 20 ml of dichloromethane, and the reaction mixture is heated at 40° C. for 2 hours. The solvent is concentrated and the residue is thoroughly stirred with diethyl ether and filtered off under a protective gas atmosphere. 1.52 g (100%) of the dihydrochloride of the title compound are obtained. m.p. 130° C.

Pyridine-2,6-dicarbobis(4-tert-butyloxycarbonylamino-1-piperidide) (14)

850 mg (4.05 mmol) of 2,6-pyridinedicarbonyl dichloride in 10 ml of dioxane are added dropwise to a suspension of 1.67 g (8.08 mmol) of tert-butyl piperidine-N-carboxylate in 0.65 ml (8.08 mmol) of pyridine, 2.8 ml (20 mmol) of triethylamine and 10 ml of dioxane. The mixture is stirred overnight at room temperature and then concentrated. 30 ml of water are added to the residue and the resulting solution is made basic (pH=11) with NaOH. It is then extracted with 3×30 ml of dichloromethane, after which the combined organic phases are dried over MgSO$_4$ and concentrated, and the residue is crystallized from diethyl ether. 2.12 g (99%) of the title compound, having a m.p. of 90° C., are obtained.

Example 5

End Product

Figure 5:
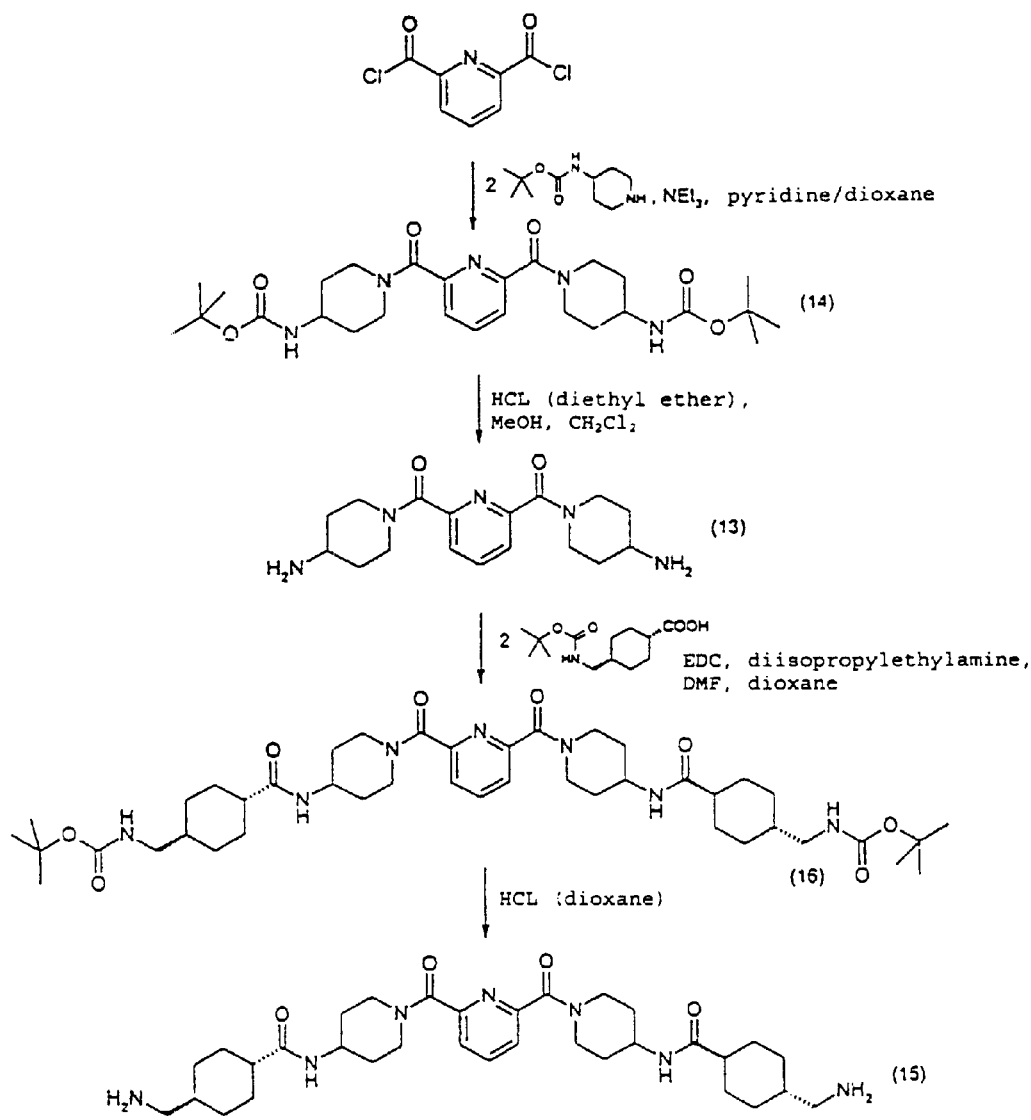

Pyridine-2,6-dicarbobis[4-(4-aminomethylcyclohexylcarbonylamino)-1-piperidide] (15) (cf. FIG. 5)

500 µl of a 4 N solution of HCl in dioxane (2.0 mmol) are added dropwise to a suspension of 160 mg (197 µmol) of pyridine-2,6-dicarbobis[4-(4-tert-butyloxycarbonylaminomethylcyclohexylcarbonylamino)-1-piperidide in 10 ml of dioxane and 2 ml of methanol, and the mixture is stirred at room temperature for 12 hours. It is then concentrated and the residue is coevaporated twice with 50 ml of diethyl ether; the crude product is then thoroughly stirred in diethyl ether. 100 mg of the title compound, having a m.p. of >250° C., are obtained.

Starting Compounds

Pyridine-2,6-dicarbobis[4-(4-tert-butyloxycarbonylaminomethylcyclohexylcarbonyl amino)-1-piperidide] (16)

350 mg (1.36 mmol) of trans-3-tert-butyloxycarbonylaminomethylcyclohexylcarboxylic acid, 240 µl (1.36 mmol) of Hunig's base, 30 mg of diaminopyridine and 260 mg (1.36 mmol) of N-(3-dimethylaminopropyl)-N'-ethylcarbodiimide hydrochloride (EDC×HCl) are added, one after the other, to a suspension of 250 mg (0.62 mmol) of pyridine-2,6-dicarbobis(4-amino-1-piperidide) dihydrochloride in 2.5 ml of DMF and 2.5 ml of dioxane. After having been stirred at room temperature for 12 hours, the reaction mixture is concentrated, after which 10 ml of water are added to the residue and the resulting solution is adjusted to pH=3 (0.1 N HCl). It is then extracted with 3×20 ml of dichloromethane, after which the combined organic phases are dried over $MgSO_4$ and concentrated, and the crude product is chromatographed through silica gel (dichloromethane/methanol=19:1). The product-containing eluate is concentrated and the residue is thoroughly stirred in diethyl ether. 230 mg (46%) of the title compound, having a m.p. of >250° C., are obtained.

Example 6

End Product

Figure 6:
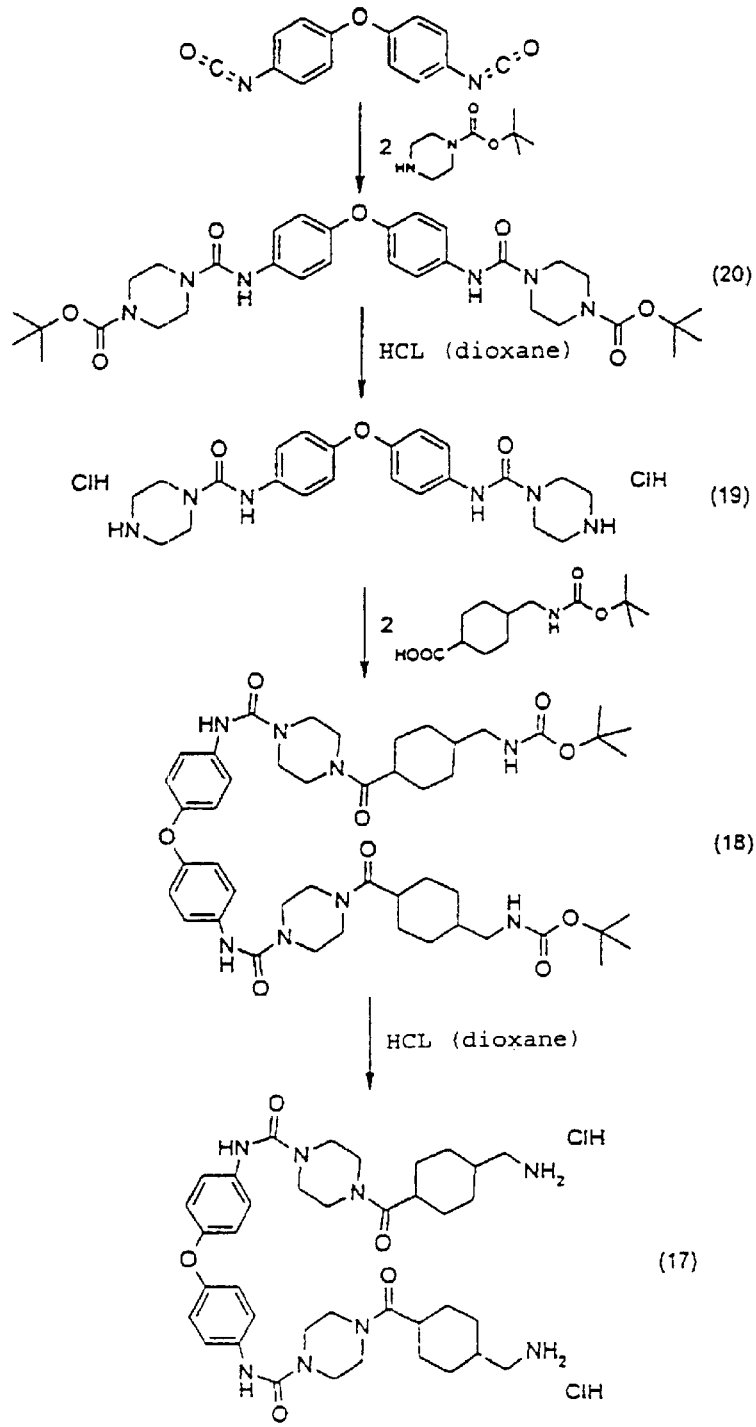

Bis{4-[4-(4-aminomethyl)cyclohexanoylpiperazin-1-yl]-carbonyl}-4,4'-diaminodiphenyl ether dihydrochloride (17) (cf. FIG. 6)

Bis{4-[4-(4-tert-butoxycarbonylaminomethyl)cyclohexanoylpiperazin-1-yl]carbonyl}-4,4'-diaminodiphenyl ether (0.18 g; 0.2 mmol) is suspended in 4.8 M HCl in dioxane (5 ml). The suspension is stirred at 40–45° C. 20 for 24 hours. After the addition of diethyl ether (25 ml), the mixture is cooled in an ice bath. The product, which has precipitated out, is filtered off with suction, washed several times with diethyl ether and dried in vacuo. Yield: 0.12 g, white amorphous solid.

MS (ESI): 703.4 (100) $MH^+$

Starting Compounds

Bis{4-(4-(4-tert-butoxycarbonylaminomethyl)cyclohexanoylpiperazin-1-yl]carbonyl}-4,4'-diaminodiphenyl ether (18)

4,4'-Bis(1-piperazinylcarbamoyl)diphenyl ether dihydrochloride (0.25 g; 0.5 mmol), Boc-tranexamic acid (0.28 g; 1.1 mmol), N-ethyldiisopropylamine (0.2 ml; 1.1 mmol) and 4-dimethylaminopyridine (5 mg) are stirred, at room temperature for 15 minutes, in dimethyl formamide (2.5 ml) and dichloromethane (2.5 ml). After the addition of N-(3-dimethylamino-propyl)-N'-ethylcarbodiimide hydrochloride (0.21 g; 1.1 mmol), the reaction mixture is stirred at 40° C. for 24 hours. The solvent is stripped off completely in vacuo. The residue is chromatographed on silica gel (dichloromethane:methanol —9:1). The product fraction is collected and the solvent is stripped off completely in vacuo. Yield: 0.18 g, white amorphous solid.

MS (ESI): 903.1 (100) $MH^+$ 4,4'-Bis(1-piperazinylcarbamoyl)diphenyl ether dihydrochloride (19)

4,4'-Bis[4-(tert-butyloxycarbonyl)-1-piperazinylcarbamoyl]diphenyl ether (6.4 g; 10.2 mmol) is suspended in 4.8 M HCl in dioxane (50 ml). The suspension is stirred at 40–45° C. for 22 hours. After the addition of diethyl ether (100 ml), the mixture is cooled in an ice bath. The product, which has precipitated out, is filtered off with suction, washed several times with diethyl ether and dried in vacuo. Yield: 4.65 g, white amorphous solid.

MS (APCI): 425.0 (100) $MH^+$ 4,4'-Bis[4-(tert-butyloxycarbonyl)-1-piperazinylcarbamoyl]diphenyl ether (20)

A solution of 4,4'-oxybis(phenyl isocyanate) (2.52 g, 10 mmol) in dichloromethane (25 ml) is added dropwise, at room temperature, to a stirred solution of 1-tert-butoxycarbonylpiperazine (4.10 g; 22 mmol) in dichloromethane (50 ml). After the addition has come to an end, the mixture is stirred at room temperature for a further 3 hours. The product, which has precipitated out, is filtered off with suction, washed several times with hexane and dried in vacuo. Yield: 6.20 g of a white amorphous solid.

MS (EI): 625.5 (12) $MH^+$; 271.2 (26); 118.2 (42); 187.1 (100)

Example 7

End Product

Figure 7:
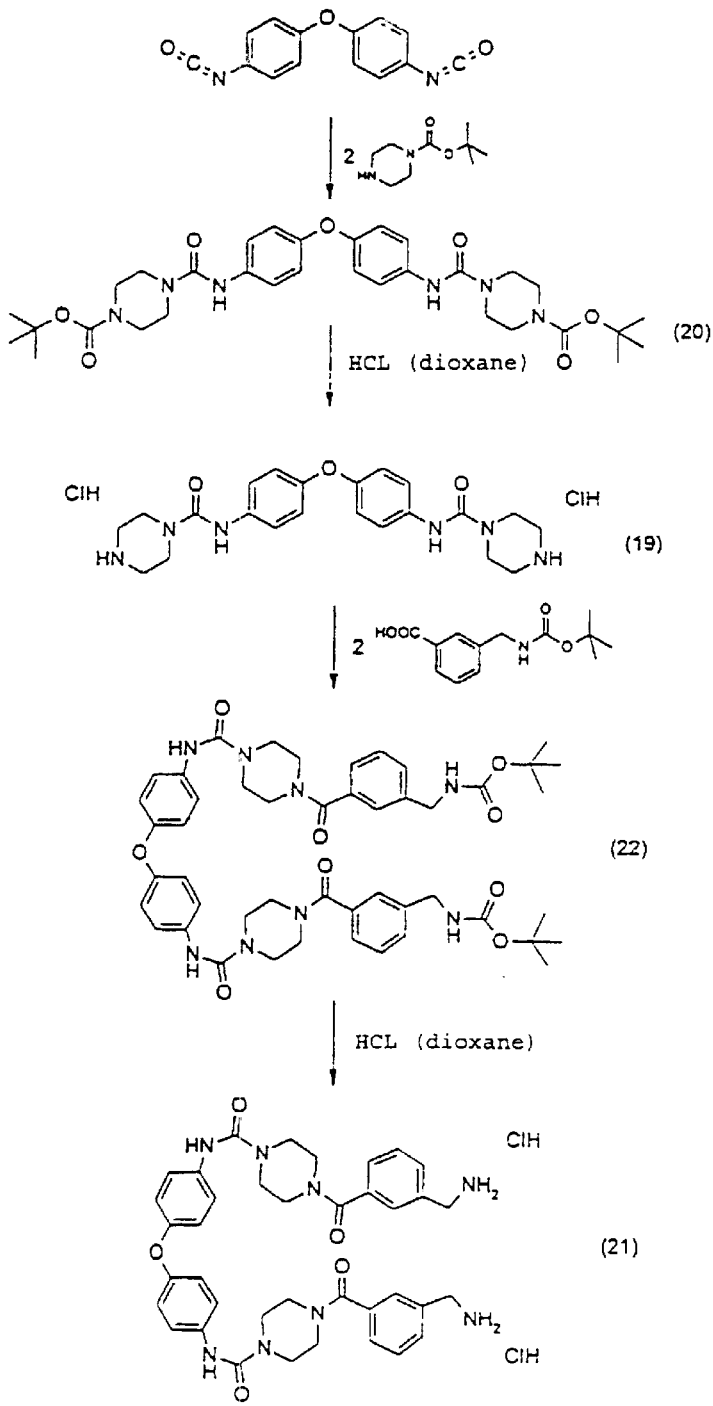

Bis{4-[4-(3-aminomethyl)benzoylpiperazin-1-yl]-carbonyl}-4,4'-diaminodiphenyl ether dihydrochloride (21) (cf. FIG. 7)

Bis{4-[4-(3-tert-butoxycarbonylaminomethyl)benzoylpiperazin-1-yl]carbonyl}-4,4'-diaminodiphenyl ether (0.31 g; 0.35 mmol) is stirred, at 40–45° C. for 24 hours, in 4.8 M HCl in dioxane (5 ml). After the addition of diethyl ether (25 ml), the mixture is cooled in an ice bath. The product, which has precipitated out, is filtered off with suction, washed several times with diethyl ether and dried in vacuo. Yield: 0.19 g, white amorphous solid.

MS (ESI): 691.2 (100) $MH^+$

Starting Compounds

Bis{4-[4-(3-tert-butoxycarbonylaminomethyl)benzoylpiperazin-1-yl]carbonyl)}4,4'-diaminodiphenyl ether (22)

4,4'-Bis(1-piperazinylcarbamoyl)diphenyl ether dihydrochloride (0.25 g; 0.5 mmol), 3-(tert-butoxycarbonylaminomethyl)benzoic acid (0.28 g; 1.1 mmol), N-ethyl-diisopropylamine (0.2 ml; 1.1 mmol) and 4-dimethylaminopyridine (30 mg) are stirred, at room temperature for 15 minutes, in dimethyl formamide (2.5 ml) and dioxane (2.5 ml). After the addition of N-(3-dimethylaminopropyl)-N'-ethylcarbodiimide hydrochloride (0.21 g; 1.1 mmol), the reaction mixture is stirred at room temperature for 24 hours. The solvent is stripped off completely in vacuo. The residue is chromatographed on silica gel (dichloromethane:methanol—9:1). The product fraction is collected and the solvent is stripped off completely in vacuo. Yield: 0.32 g, viscous oil.

MS (ESI): 890.8, M$^+$; 791.2, MH-Boc$^+$

Example 8

End Product

Figure 8:
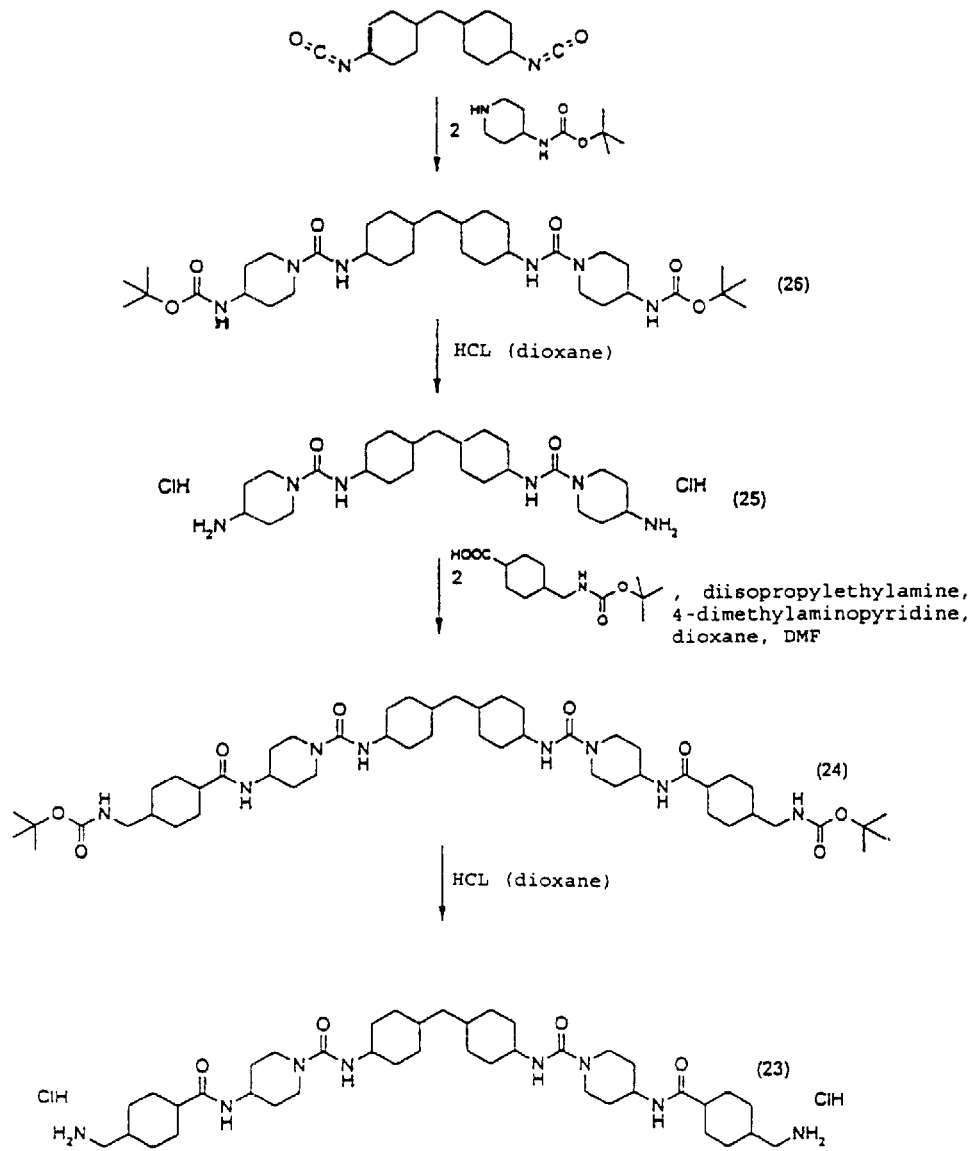

Di{4-[4-(4-aminomethyl)cyclohexanoylamino]
piperidin-1-ylcarbamoyl}cyclohexylmethane
dihydrochloride (23) (cf. FIG. 8)

Di{4-[4-(4-tert-butoxycarbonylaminomethyl)
cyclohexanoylamino]piperidin-1-
ylcarbamoyl}cyclohexylmethane (0.65 g; 0.7 mmol) is stirred, at 40–45° C. for 24 hours, in 4.8 M HCl in dioxane (7 ml). After the addition of diethyl ether (50 ml), the mixture is cooled in an ice bath. The product, which has precipitated out, is filtered off with suction, washed several times with diethyl ether and dried in vacuo. Yield: 0.26 g, white amorphous solid.

MS (ESI): 741.5 (100) MH$^+$

Starting Compounds

Di{4-[4-(4-tert-butoxycarbonylaminomethyl)
cyclohexanoylamino]piperidin-1-
ylcarbamoyl}cyclohexylmethane (24)

Di [4-(4-aminopiperidin-1-ylcarbamoyl)]cyclohexylmethane dihydrochloride (0.54 g; 1.0 mmol), Boc-tranexamic acid (0.57 g; 2.2 mmol), N-ethyldiisopropylamine (0.38 ml; 2.2 mmol) and 4-dimethylaminopyridine (30 mg) are stirred, at room temperature for 15 minutes, in dimethyl formamide (5 ml) and dioxane (5 ml). After the addition of N-(3-dimethylaminopropyl) -N'-ethylcarbodiimide hydrochloride (0.43 g; 2.2 mmol), the reaction mixture is stirred at 40° C. for 48 hours. The solvent is completely stripped off in vacuo. The residue is chromatographed on silica gel (dichloromethane:methanol—9:1). The product fraction is collected and the solvent is stripped off completely in vacuo. Yield: 0.65 g, viscous oil, which was subjected to further reaction without any characterization.

Di[4-(4-aminopiperidin-1-ylcarbamoyl)]
cyclohexylmethane dihydrochloride (25)

Di{4-[4-(tert-butoxycarbamoyl)piperidin-1-yl-carbamoyl]}cyclohexylmethane (4.90 g; 7.0 mmol) is suspended in 4.8 M HCl in dioxane (50 ml). The suspension is stirred at 40–45° C. for 48 hours. After the addition of diethyl ether (100 ml), the mixture is cooled in an ice bath. The product, which has precipitated out, is filtered off with suction, washed several times with diethyl ether and dried in vacuo. Yield: 4.10 g, white amorphous solid.

MS(EI): 463.4 (100) MH$^+$

Di{4-[4-(tert-butoxycarbamoyl)piperidin-1-yl-carbamoyl]}cyclohexylmethane (26)

A solution of dicyclohexylmethane-4,4'-diisocyanate (1.90 g; 7.3 mmol) in dichloromethane (10 ml) is added dropwise, at room temperature, to the stirred solution of 4-tert-butoxycarbamoylpiperidine (3.20 g; 16.0 mmol) in dichloromethane (30 ml). After the addition has come to an end, the mixture is stirred at room temperature for a further three hours. The product, which has precipitated out, is filtered off with suction, washed several times with hexane and dried in vacua. Yield: 4.10 g, white amorphous solid.

MS(ESI) : 685.3 (57) MNa$^+$; 663.2 (100) MH$^+$

Example 9

Figure 9:
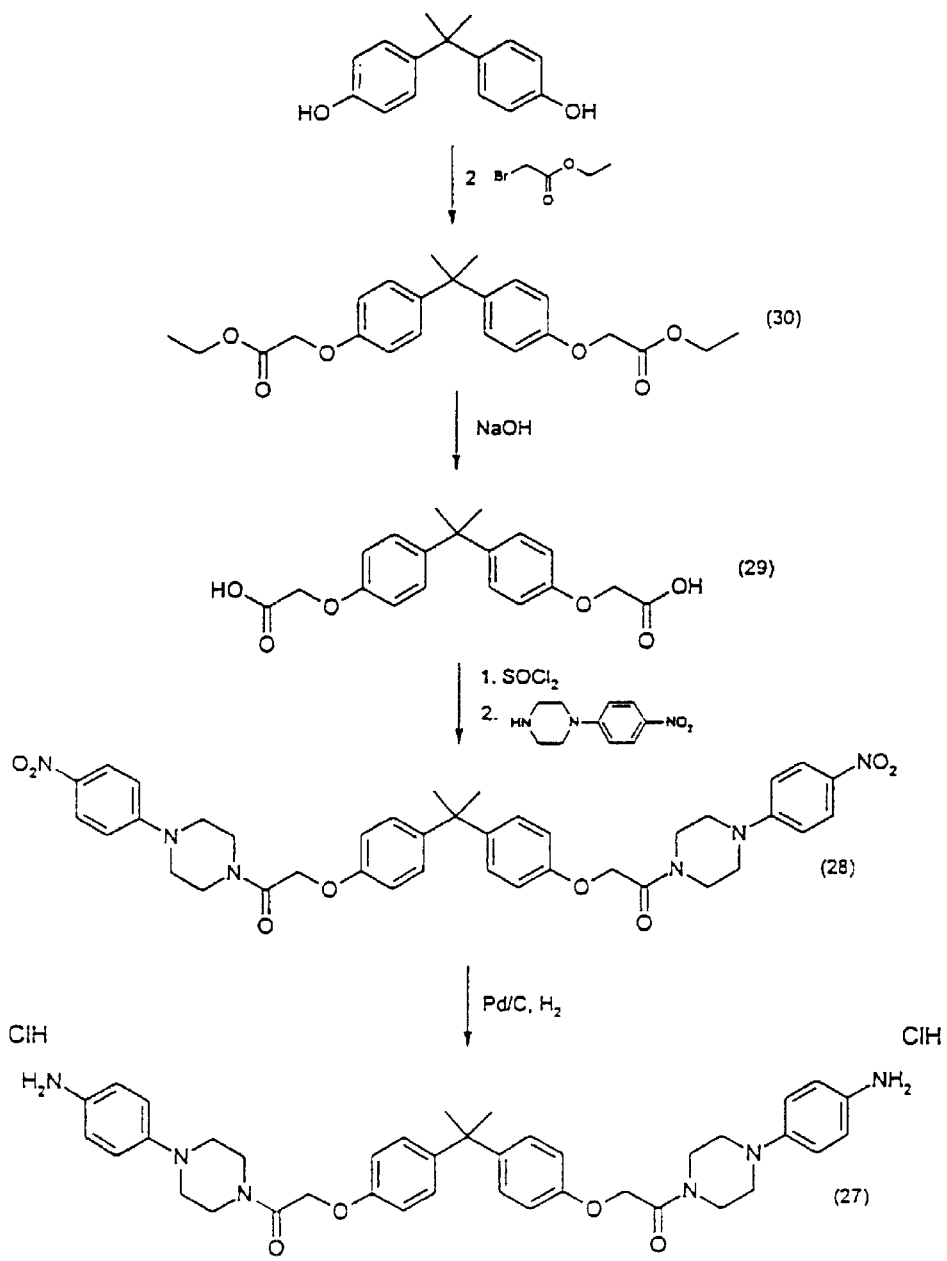

End Product 2,2-Bis{4-[4-(4-aminophenyl)-1-
piperazinylcarbonylmethoxy]phenyl}propane
dihydrochloride (27) (cf. FIG. 9)

0.65 g of 2,2-bis{4-[4-(4-nitrophenyl)-1-piperazinylcarbonylmethoxy]phenyl}propane is dissolved in 60 ml of glacial acetic acid, and 0.2 g of palladium charcoal (10%) is added. The mixture is hydrogenated in a bypass apparatus until the starting product can no longer be detected (TLC). The catalyst is filtered off with suction through celite and the filtrate is evaporated down to dryness in vacuo on a rotary evaporator. The residue is dissolved in dichloromethane and the solution is washed with NaHCO$_3$ solution, dried over Na$_2$SO$_4$, filtered and concentrated once again. The residue is chromatographed through a silica gel column using a mixture consisting of ethyl acetate/methanol/NH$_4$OH (25%), in the ratio 90:8:2, as the mobile phase. The chromatographically pure fractions are combined and concentrated, and the residue is dissolved in dichloromethane. Following the addition of ethereal hydrochloric acid, the solution is concentrated and the residue is subsequently distilled twice with dichloromethane and then triturated with ethyl acetate/isopropanol. The precipitate is filtered off with suction, washed and then dried under high vacuum. 0.32 g of the title compound, having a m.p., with decomposition, from 182° C., is obtained.

Starting Compounds 2,2-Bis{4-[4-(4-nitrophenyl)-1-
piperazinylcarbonylmethoxy]phenyl}propane (28)

2.5 g of 4-[4-carboxymethoxyphenyl)-1-methylethyl]-phenoxyacetic acid are suspended in toluene, and 1.6 ml of thionyl chloride are added. The mixture is heated under reflux for 5 hours and, after cooling, is concentrated on a rotary evaporator. The residue is subsequently distilled twice with toluene and the resulting crude diacid chloride is then dissolved in 50 ml of abs. dioxane. 2.95 g of 1-(4-nitrophenyl)piperazine, 2 ml of triethylamine and a spatula tip of 4-dimethylaminopyridine are added one after the other. The mixture is stirred at 50° C. for 2.5 h. Following cooling, water is added to the mixture and the pH is adjusted to 9 with dilute sodium hydroxide solution. The product, which has separated out, is caused to crystallize by grinding, and the crystals are then filtered off with suction, washed with water and dried over calcium chloride. 4.7 g of the title compound, having a m.p., with decomposition, from 165° C., are obtained.

4-[1-(4-Carboxymethoxyphenyl)-1-methylethyl]
phenoxyacetic acid (29)

6.7 g of ethyl 4-[1-(4-ethoxycarbonylmethoxyphenyl)-1-methylethyl]phenoxyacetate are dissolved in 20 ml of methanol, and 16.7 g of 10% strength sodium hydroxide solution are added. The mixture is heated to boiling under reflux for 3 hours, after which it is cooled down and the methanol is then distilled off on a rotary evaporator. The residue is diluted with water and acidified to pH 2 with 2 N HCl; the colorless precipitate is then filtered off with suction, washed with water and dried in vacuo over calcium chloride. 5.5 g of the title compound, having a m.p. of 177–179° C., are obtained.

Ethyl 4-[1-(4-ethoxycarbonylmethoxyphenyl)-1-methyl-ethyl]phenoxyacetate (30)

A mixture of 10 g of 4,4'-isopropylidenediphenol, 10.7 ml of ethyl bromoacetate, 15.2 g of potassium carbonate and 1 spatula tip of 18-crown-6 in 180 ml of acetone is heated to boiling under reflux for 4 hours. The solid is then removed by filtering off with suction and the filtrate is concentrated in vacuo and 100 ml of diisopropyl ether are added to the residue. The precipitate is filtered off with suction, washed with a little diisopropyl ether and dried. 15.5 g of the title compound, having a m.p. of 69–71° C., are obtained.

Example 10

End Product

Figure 10:
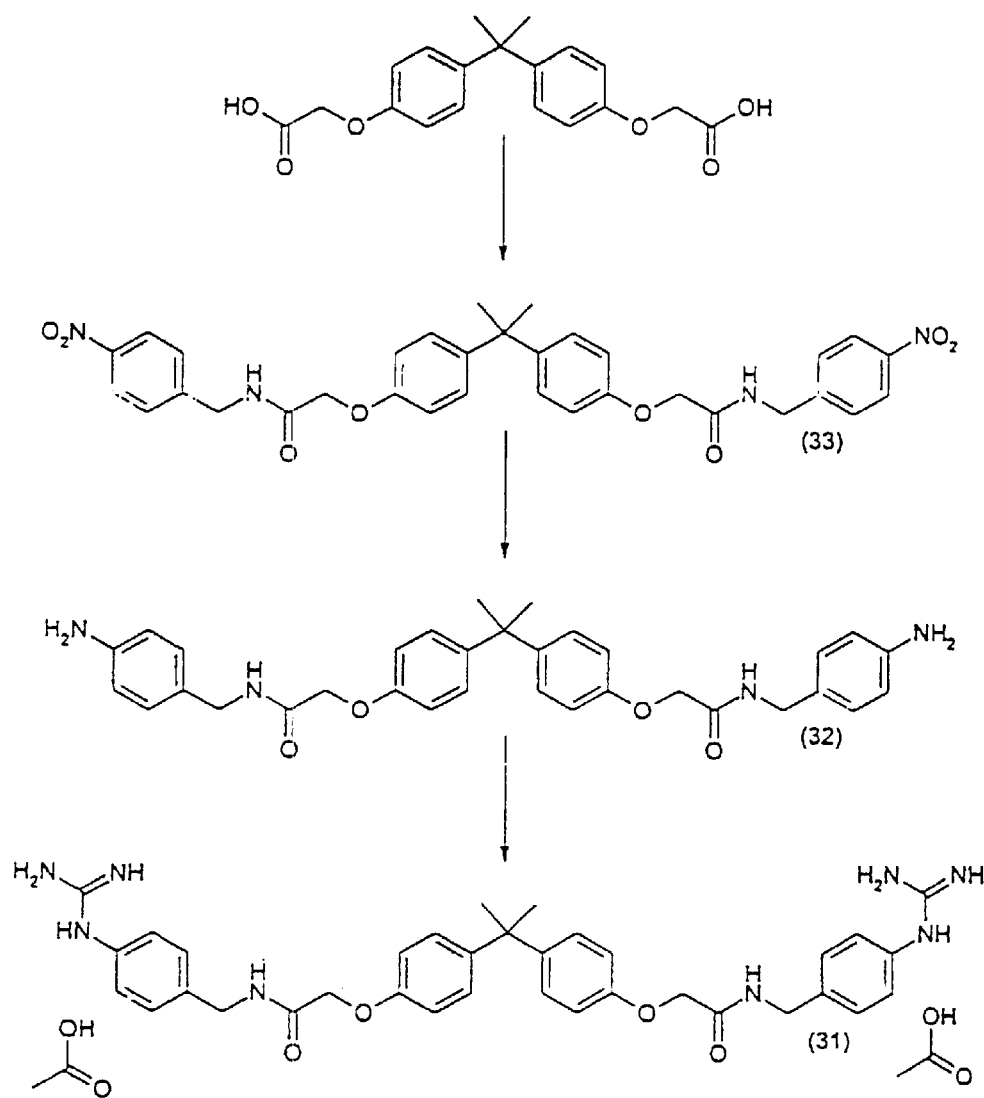

2,2-Bis-[4-(4-guanidinylbenzylamino) carbonylmethoxyphenyl]propane dihydroacetate (31) (cf. FIG. 10)

0.88 g of 1,3-bis(benzyloxycarbonyl)-2-methylisothiourea, 0.68 g of mercury(II) chloride and 0.69 g of triethylamine are added, one after the other, while stirring, to 0.63 g of 2,2-bis-[4-(4-aminobenzylamino)-carbonylmethoxyphenyl]propane in 10 ml of abs. DMF. The mixture is stirred at room temperature for 3 h and is then diluted with ethyl acetate; the precipitate which results is removed by filtering off with suction and the filtrate is washed once with a 5% strength soda solution and twice with water. The solution is dried over magnesium sulfate and filtered with suction, and the filtrate is evaporated to dryness in vacuo. The oil is chromatographed through a silica gel column using a mixture consisting of dichloromethane/ethanol, 95:5. The chromatographically pure fractions are combined and concentrated, and the residue (0.9 g) is dissolved in a mixture consisting of 60 ml of tetrahydrofuran, 3 ml of methanol and 1 ml of glacial acetic acid. After 0.3 g of palladium charcoal (10%) has been added, the mixture is hydrogenated in a bypass apparatus until the starting compound can no longer be detected. The catalyst is removed by filtering off with suction and the filtrate is evaporated to dryness. The viscous oil which remains is stirred up with THF and the resulting precipitate is filtered off with suction, washed with THF and diethyl ether and dried in vacuo at 80° C. 0.35 g of the title compound, having a m.p. of 135° (decomposition), is obtained.

Starting Compounds

2,2-Bis-[4-(4-aminobenzylamino) carbonylmethoxyphenyl]-propane (32)

1.8 g of 2,2-bis-[4-(4-nitrobenzylamino) carbonylmethoxyphenyl]propane are dissolved in 300 ml of THF and, after addition of 0.5 g of palladium charcoal (10%), are hydrogenated in a bypass apparatus until the starting compound can no longer be detected (TLC). After the catalyst has been filtered off with suction, the filtrate is concentrated to dryness in vacuo and the residue is chromatographed through a silica gel column using a mixture of dichloromethane/ethanol, 95:5. The chromatographically pure fractions are combined and concentrated, and the residue is dried under high vacuum. 1.05 g of the title compound are obtained in the form of a solidified foam.

2,2-Bis-[4-(4-nitrobenzylamino) carbonylmethoxyphenyl]-propane (33)

1.5 ml of thionyl chloride are added to 2 g of 4-[1-(4-carboxymethoxyphenyl)-1-methylethyl]phenoxyacetic acid in 100 ml of toluene, and the mixture is heated to boiling under reflux for 5 h. After cooling, it is concentrated on a rotary evaporator and the residue is subsequently distilled twice with toluene. The resulting diacid chloride is dissolved in 40 ml of abs. dioxane, after which 2.2 g of 4-nitrobenzylamine hydrochloride are added; 3.5 ml of triethylamine are then added dropwise. The mixture is stirred at 50° C. for 2 h and then concentrated in vacuo. The precipitate which is obtained after adding water is filtered off with suction and dried in vacuo and, for further purification, chromatographed through a silica gel column using ethylacetate. The chromatographically pure fractions are combined, concentrated and dried. 1.25 g of the title compound are obtained as a solidified foam.

Example 11

End Product

Figure 11:
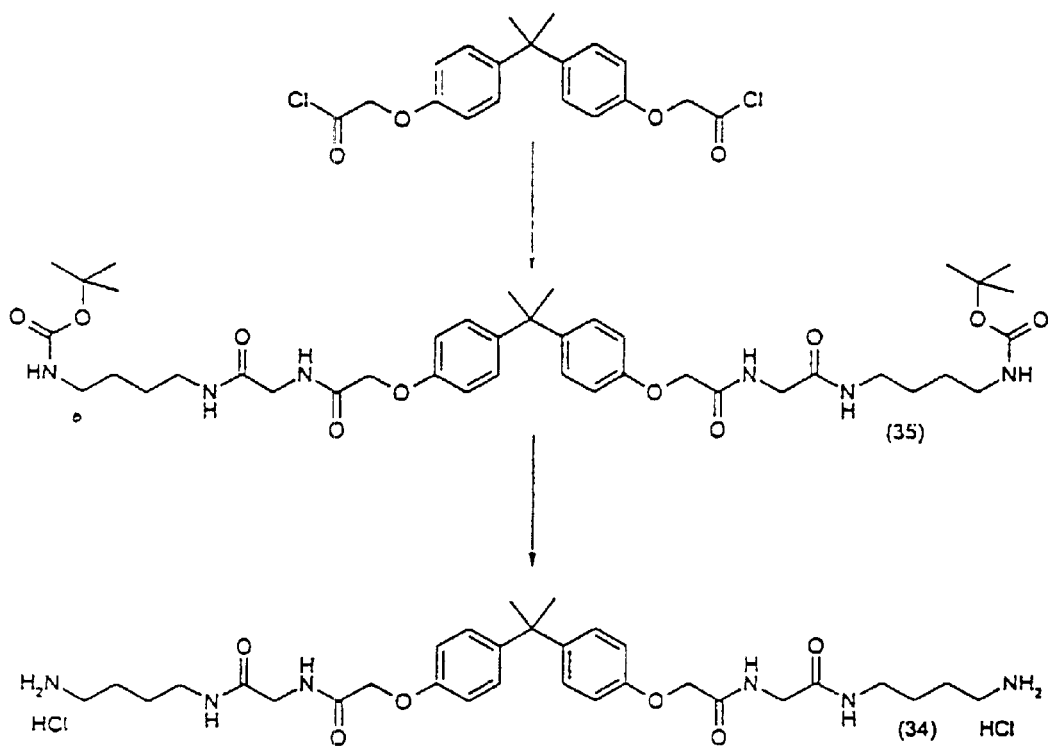

5 2,2-Bis-[4-(10-amino-3,6-diaza-2,5-dioxodecyloxy)-phenyl]propane dihydrochloride (34) (cf. FIG. 11)

0.77 g of 2,2-bis-{4-[10-(tert-butoxycarbonylamino)-3,6-diaza-2,5-dioxodecyloxy]phenyl}propane is dissolved in 10 ml of abs. dioxane, and 2 ml of an approx. 4.8 M solution of hydrogen chloride in dioxane are added to this solution. The mixture is stirred overnight and the resulting precipitate is then filtered off with 15 suction, washed with dioxane and then with diethyl ether and dried in vacuo at 80° C. 0.58 g of the title compound, having a m.p. of 173° C. (decomposition), is obtained.

Starting Compounds

2,2-Bis-[4-(10-(tert-butoxycarbonylamino)-3,6-diaza-2,5-dioxodecyloxy]phenyl}propane (35)

0.67 g of 2,2-bis-(4-chlorocarbonylmethoxyphenyl)-propane (prepared in analogy with Example 33) in 5 ml of abs. dioxane is added dropwise, while stirring, to a solution of 0.85 g of N-[4-(tert-butoxycarbonylamino)butyl] glycineamide and 0.42 g of triethylamine in 10 ml of abs. dioxane. The mixture is stirred overnight and concentrated in vacuo, and the residue is partitioned between water and ethyl acetate. The organic phase is washed twice with water, dried over magnesium sulfate and concentrated. The residue is chromatographed through a silica gel column using a mixture of dichloromethane/ethanol, 95:5. The chromatographically pure fractions are combined and concentrated, and the residue is crystallized using diethyl ether/2-propanol. It is filtered off with suction, washed with diethyl ether and dried in vacuo. 0.77 g of the title compound, having a m.p. of 59° C. (decomposition), is obtained.

Example 12

End Product

Figure 12:
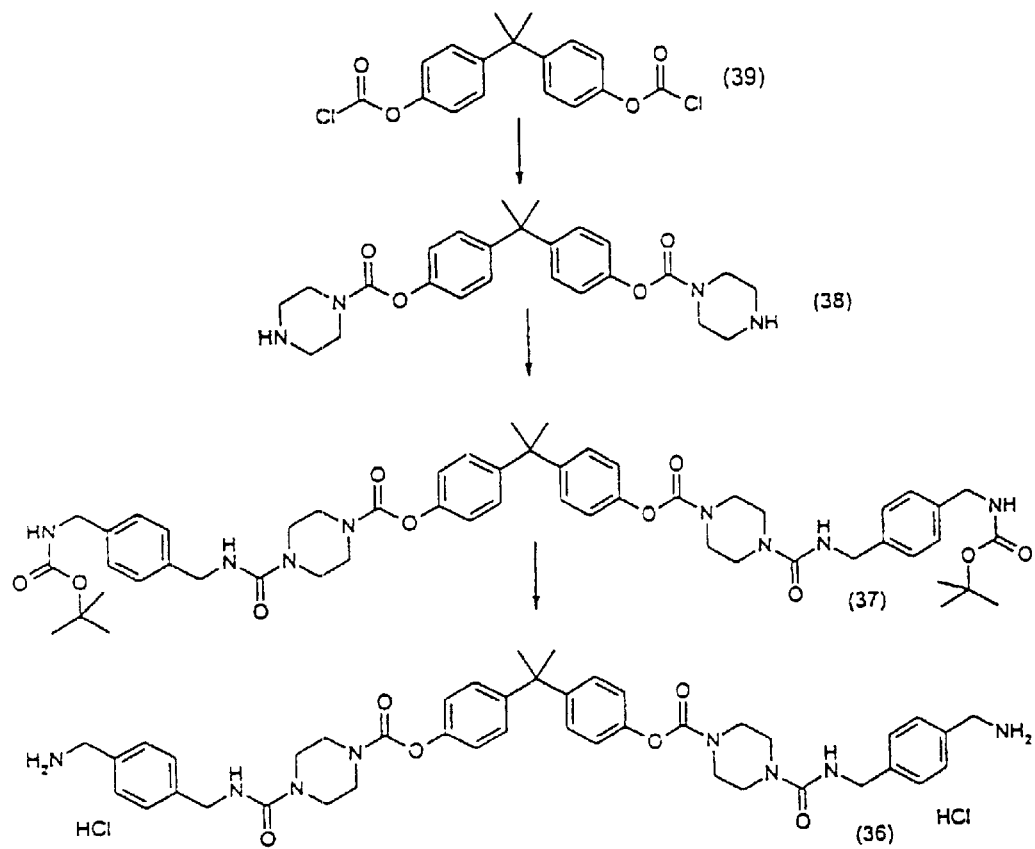

2,2-Bis-{4-[4-(4-aminomethylbenzylcarbamoyl)-1-piperazinylcarbonyloxy]phenyl}propane dihydrochloride (36) (cf. FIG. 12)

0.14 g of 2,2-bis-{4-[4-(4-tert-butoxycarbonylaminomethylbenzylcarbamoyl)-1- piperazinylcarbonyloxy]-phenyl}propane is dissolved in 2 ml of abs. dioxane, and 2 ml of an approx. 20% solution of hydrogen chloride in dioxane is added to this solution. The mixture is stirred overnight and the precipitate is filtered off with suction, washed twice with diethyl ether and dried in vacuo. 0.08 g of the title compound, having a m.p. of from 250° C. (decomposition), is obtained.

Starting Compounds 2,2-Bis-{4-[4-(4-tert-butoxycarbonylaminomethylbenzylcarbamoyl)-1-piperazinylcarbonyloxy]phenyl}propane (37)

0.2 g of 2,2-bis[4-(1-piperazinylcarbonyloxy)phenyl]propane dihydrochloride and 0.66 ml of diisopropylethylamine are dissolved in 5 ml of dichloromethane, and 0.4 ml of a 20% strength solution of phosgene in toluene is then added to this solution. After the mixture has been stirred at room temperature for 30 min, 0.18 g of 4-(tert-butoxycarbonylaminomethyl)-benzylamine is added and the mixture is stirred for a further 30 min. Water is then added and the phases are separated; the organic phase is then washed a further two times with water. After the organic phase has been dried over magnesium sulfate, it is concentrated on a rotary evaporator. The residue is chromatographed through a silica gel column using dichloromethane/methanol, 95:5, as the mobile phase. The chromatographically pure fractions are combined and evaporated to dryness in vacuo. 0.17 g of the title compound is obtained as a solidified foam.

2,2-Bis[4-(1-piperazinylcarbonyloxy)phenyl]propane dihydrochloride (38)

8.3 g of 2,2-bis[4-(4-tert-butoxycarbonyl-1-piperazinylcarbonyloxy)phenyl]propane dihydrochloride are dissolved in 50 ml of abs. dioxane, and 9.5 ml of an approx. 20% solution of hydrogen chloride in dioxane are added to this solution while stirring. The mixture is stirred overnight, after which it is diluted with toluene and the precipitate is filtered off with suction. After drying in vacuo, 5.7 g of the title compound, having a m.p. of from 200° C. (decomposition), are obtained.

2,2-Bis[4-(4-tert-butoxycarbonyl-1-piperazinylcarbonyloxy)phenyl]propane (39)

5 g of bisphenol A bis(chloroformate) are dissolved in 50 ml of dichloromethane, and 7.3 ml of diisopropylethylamine and 6.6 g of 1-tert-butoxycarbonylpiperazine are added while cooling with ice. The mixture is stirred at room temperature for 1 h and then extracted three times with an ice-cold 0.5 N solution of hydrochloric acid and twice with 1 N sodium hydroxide solution. After having been dried with magnesium sulfate, it is then evaporated on a rotary evaporator and the solid is dried in vacuo. 8.4 g of the title compound, having a m.p. of 171–172° C., are obtained.

Commercial Utility

As inhibitors of human tryptase, the compounds according to the invention have useful pharmacological properties which make them commercially utilizable. Human tryptase is a serine protease which is the main protein in human mast cells. Tryptase comprises four closely related enzymes ($\alpha$, I, II/$\beta$, III; 90 to 98% sequence identity) (cf. Miller et al., J. Clin. Invest. 84 (1989) 1188–1195; Miller et al., J. Clin. Invest. 86 (1990) 864–870; Vanderslice et al., Proc. Natl. Acad. Sci., USA 87 (1990) 3811–3815). Except for $\alpha$-tryptase (Schwartz et al., J. Clin. Invest. 96 (1995) 2702–2710; Sakai et al., J. Clin. Invest. 97 (1996) 988–995) the enzymes are activated intracellularly and stored in catalytically active form in secretory granules. Compared with other known serine proteases, such as, for example, trypsin or chymotripsin, tryptase has some special properties (Schwartz et al., Methods Enzymol. 244, (1994), 88–100; G. H. Caughey, "Mast cell proteases in immunology and biology". Marcel Dekker, Inc. New York, 1995). Tryptase from human tissue has a noncovalently-linked tetrameric structure which has to be stabilized by heparin or other proteoglycanes to be proteolytically active. Together with other inflammatory mediators, such as, for example, histamine and proteoglycanes, tryptase is released when human mast cells are activated. Because of this, tryptase is thought to play a role in a number of disorders, in particular in allergic and inflammatory disorders, firstly because of the importance of the mast cells in such disorders and secondly because an increased tryptase concentration was observed in a number of disorders of this type. Thus, tryptase is associated, inter alia, with the following diseases; acute and chronic (in particular inflammatory and allergen-induced) airway disorders of various origins (for example bronchitis, allergic bronchitis, bronchial asthma, COPD); interstitial lung disorders; disorders based on allergic reactions of the upper airways (pharynx, nose) and the adjacent regions (for example paranasal sinuses, conjunctivae), such as, for example, allergic conjunctivitis and allergic rhinitis; disorders of the arthritis type (for example rheumatoid arthritis); autoimmune disorders, such as multiple sclerosis; furthermore periodontitis, anaphylaxis, interstitial cystitis, dermatitis, psoriasis, sclerodermia/systemic sclerosis, inflammatory intestinal disorders (Crohns disease, inflammatory bowel disease) and others. In particular, tryptase seems to be connected directly to the pathogenesis of asthma (Caughey, Am. J. Respir. Cell Mol. Biol. 16 (1997), 621–628; R. Tanaka, "The role of tryptase in allergic inflammation" in: Protease Inhibitors, IBC Library Series, 1979, Chapter 3.3.1–3.3.23).

A further subject of the invention relates to the compounds according to the invention for use in the treatment and/or prophylaxis of diseases, in particular the diseases mentioned.

The invention likewise relates to the use of the compounds according to the invention for preparing medicaments which are employed for the treatment and/or prophylaxis of the diseases mentioned.

Medicaments for the treatment and/or prophylaxis of the diseases mentioned, which contain one or more of the compounds according to the invention, are furthermore subject of the invention.

The medicaments are prepared by processes which are known per se to the person skilled in the art. As medicaments, the compounds according to the invention (=active compounds) are either employed as such, or preferably in combination with suitable pharmaceutical excipients, for example in the form of tablets, coated tablets, capsules, suppositories, patches, emulsions, suspensions, gels or solutions, the active compound content advantageously being between 0.1 and 95%.

The person skilled in the art is familiar on the basis of his/her expert knowledge with the excipients which are suitable for the desired pharmaceutical formulations. In addition to solvents, gel-forming agents, ointment bases and other active compound vehicles, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this purpose, they are either administered directly as a powder (preferably in micronized form) or by nebulization of solutions or suspensions which contain them. With respect to the preparations and administration forms, reference is made, for example, to the details in European patent 163 965.

For the treatment of dermatoses, the compounds according to the invention are in particular used in the form of those medicaments which are suitable for topical administration. For the preparation of the medicaments, the compounds according to the invention (=active compounds) are preferably mixed with suitable pharmaceutical excipients and further processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by processes known per se. The dosage of the active compounds in the case of systemic therapy (p.o. or i.v.) is between 0.1 and 10 mg per kilogram and day.

Biological Investigations

The documented pathophysiological effects of mast cell tryptase are brought about directly by the enzymatic activity of the protease. Accordingly, they are reduced or blocked by inhibitors which inhibit the enzymatic activity of the tryptase. The equilibrium dissociation constant $K_i$ of the enzyme-inhibitor complex is a suitable measure of the affinity of a reversible inhibitor for the target protease. This $K_i$ value can be determined by measuring the effect of the inhibitor on the tryptase-induced cleavage of a chromogenic peptide-p-nitroanilide substrate or a fluorogenic peptide-aminomethylcoumarin substrate.

Methodology

The dissociation constants of the tryptase-inhibitor complexes are determined under equilibrium conditions in accordance with the general recommendations of Bieth (Bieth J G, Pathophysiological interpretation of kinetic constants of protease inhibitors, Bull. Europ. Physiopath. Resp. 16:183–195, 1980) and the methods of Sommerhoff et al. (Sommerhoff C P et al., A. Kazal-type inhibitor of human mast cell tryptase: Isolation from the medical leech Hirudo medicinalis, characterization, and sequence analysis, Biol. Chem. Hoppe-Seyler 375: 685–694, 1994).

Human tryptase is prepared in a pure state from lung tissue; the specific activity of the isolated protease, determined by means of titration, is normally 85% of the theoretical value. Constant quantities of tryptase are incubated with increasing quantities of the inhibitors in the presence of 50 µg of heparin/ml for stabilizing the protease. After the equilibrium has been established between the reaction partners, the remaining enzyme activity is determined after adding the peptide-p-nitroanilide substrate tos-Gly-Pro-Arg-pNA, the cleavage of which is monitored at 405 nm over a period of 3 min. Alternatively, the residual enzymic activity can also be determined using fluorogenic substrates. The apparent dissociation constants $K_{iapp}$ (i.e. in the presence of substrate) are subsequently ascertained by nonlinear regression by fitting the enzyme rates to the general equation for reversible inhibitors (Morrison J F, Kinetics of the reversible inhibition of enzyme-catalysed reactions by tight-binding inhibitors, Biochim. Biophys. Acta 185, 269-286, 1969):

$$V_1/V_0 = 1 - \{E_t + I_t + K_{iapp} - [(E_t + I_t + K_{iapp})^2 - 4E_t I_t]^{1/2}\}/2E_t$$

In this equation, $V_1$ and $V_0$ are the rates in the presence and absence of the inhibitor, respectively, and $E_t$ and $I_t$ are the concentrations of the tryptase and of the inhibitor.

The apparent dissociation constants which were determined for the compounds according to the invention are given in Table A below, in which the numbers of the compounds correspond to the numbers of the compounds in the examples.

TABLE A

| Inhibition of human tryptase | |
|---|---|
| Compound | $K_{iapp}$ (µM) |
| 1 | 3 |
| 11 | 0.03 |
| 15 | 3 |
| 17 | 22 |
| 21 | 0.1 |
| 23 | 0.8 |
| 31 | 0.2 |
| 34 | 2 |
| 36 | 0.028 |

What is claimed is:
1. A compound of formula I

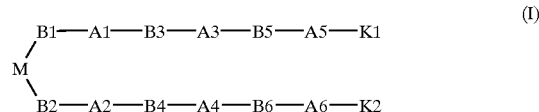

(I)

in which
A1 and A2 are each independently selected from the group consisting of —O— or —NH—C(O)—,
A3 and A4 are each independently selected from the group consisting of —C(O)—NH— or

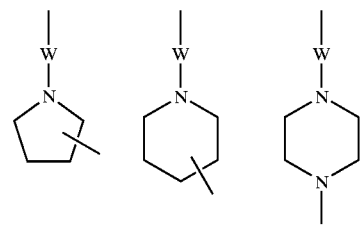

where W is the group —C(O)— or a bond,
A5 and A6 are each independently selected from the group consisting of —C(O)—, —C(O)—NH—, —NH—C(O)— or a bond,
M is selected from one of the following groups

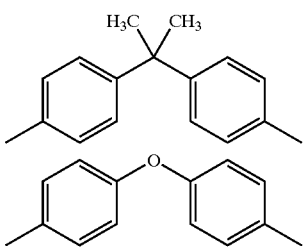

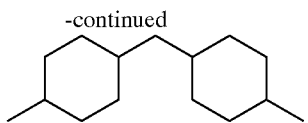

K1 is -B7-(C(O))$_m$-B9-X1 or -B7-(C(O))$_m$-B9-Z1-B11-X1,

K2 is -B8-(C(O))$_p$-B10-X2 or -B8-(C(O))$_p$-B10-Z2-B12-X2 B1, B2, B3, B4, B5 and B6 are each independently selected from the group consisting of a bond or —CH$_2$—, B7, B8, B9, B10, B11 and B12 are each independently selected from the group consisting of a bond or 1–2C-alkylene, m is 0 or 1, p is 0 or 1, X1 and X2 are each independently selected from the group consisting of amino, amidino or guanidino, Z1 and Z2 are each independently selected from the group consisting of 1,4-phenylene, 1,3-phenylene, 1,4-cyclohexylene or 1,4-piperazinylene, and in which 24 to 40 bonds must be present on the direct route between the terminal nitrogen atoms, and A pharmaceutically acceptable salt of said compound with all those compounds being excluded in which at least one to twelve of the variables B1, B2, B3, B4, B5, B6, B7, B8, B9, B10, B11 or B12 is a bond resulting in the direct linkage of two heteroatoms or two carbonyl groups.

2. A compound of claim 1, wherein

A5 and A6 are each independently selected from the group consisting of —C(O)—, —NH—C(O)— or a bond, M is selected from one of the following groups

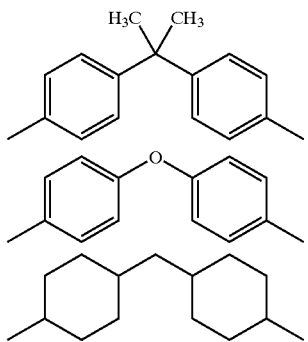

wherein

K1 is -B7-(C(O))$_m$-B9-Z1-B11-X1,

K2 is -B8-(C(O))$_p$-B 10-Z2-B12-X2,

B1, B2, B3, B4, B5 and B6 are each independently selected from the group consisting of a bond or —CH$_2$—, and B7, B8, B9, B10, B11 and B12 are each independently selected from the group consisting of a bond or —CH$_2$—.

3. A compound of claim 1, wherein the compound is:

bis{4-[4-(4-aminomethylcyclohexanoyl)piperazin-1-yl]carbonyl}-4,4'-diaminodiphenyl ether, bis{4-[4-(3-aminomethyl)benzoylpiperazin-1-yl]carbonyl}-4,4'-diaminodiphenyl ether, di{4-[4-(4-aminomethyl)cyclohexanoylamino]piperidin-1-ylcarbamoyl}cyclohexylmethane, 2,2-bis[4-(4-guanidinylbenzylamino)carbonylmethoxyphenyl]propane, 2,2-bis[4-(10-amino-3,6-diaza-2,5-dioxodecyloxyphenyl]propane or 2,2-bis{4-[4-(4-aminomethylbenzylcarbamoyl)-1-piperazinylcarbonyloxy]phenyl}propane, or a salt thereof.

4. A method of treating a disease susceptible to tryptase inhibition, said method comprising administering to a patient afflicted with such a disease a tryptase inhibiting amount of a compound of formula I.

5. A method according to claim 4, wherein the disease susceptible to tryptase inhibition is asthma.

6. A method according to claim 4, wherein the disease susceptible to tryptase inhibition is inflammatory bowel disease.

7. A method according to claim 4, wherein the disease susceptible to tryptase inhibition is psoriasis.

8. A method according to claim 4, wherein the disease susceptible to tryptase inhibition is rhinitis.

9. A method of producing a medicament for the treatment of respiratory disorders comprising: combining the compound of claim 1 with one or more suitable pharmaceutical excipients, wherein the compound of formula I is in an amount effective to treat respiratory disorders.

10. A pharmaceutical composition suitable for treating respiratory diseases comprising the compound of claim 1 in an amount effective to treat respiratory disorders and a pharmaceutical excipient.

* * * * *